US008124094B2

(12) United States Patent
Kim et al.

(10) Patent No.: US 8,124,094 B2

(45) **Date of Patent: *Feb. 28, 2012**

(54) IMMUNOGLOBULIN FC FRAGMENT MODIFIED BY NON-PEPTIDE POLYMER AND PHARMACEUTICAL COMPOSITION COMPRISING THE SAME

(75) Inventors: Young Min Kim, Youngin-si (KR); Sung Min Bae, Seoul (KR); Dae Jin Kim, Seoul (KR); Dae Hae Song, Seoul (KR); Chang Ki Lim, Suwon-si (KR); Se Chang Kwon, Seoul (KR); Gwan Sun Lee, Seoul (KR)

(73) Assignee: Hanmi Holdings Co., Ltd., Seoul (KR)

( * ) Notice: Subject to any disclaimer, the term of this patent is extended or adjusted under 35 U.S.C. 154(b) by 672 days.

This patent is subject to a terminal disclaimer.

(21) Appl. No.: 11/910,962

(22) PCT Filed: Apr. 28, 2005

(86) PCT No.: PCT/KR2005/001233

§ 371 (c)(1),
(2), (4) Date: Oct. 8, 2007

(87) PCT Pub. No.: WO2006/107124

PCT Pub. Date: Oct. 12, 2006

(65) Prior Publication Data

US 2009/0053246 A1 Feb. 26, 2009

(30) Foreign Application Priority Data

Apr. 8, 2005 (KR) ........................ 10-2005-0029666

(51) Int. Cl.
*A61K 39/00* (2006.01)

(52) U.S. Cl. ................ 424/178.1; 424/179.1; 424/183.1

(58) Field of Classification Search ........................ None
See application file for complete search history.

(56) References Cited

U.S. PATENT DOCUMENTS

| | | | | |
|---|---|---|---|---|
| 6,458,355 | B1 | 10/2002 | Hsei et al. | |
| 6,548,644 | B1 | 4/2003 | Pettit | |
| 6,656,728 | B1 | 12/2003 | Kavanaugh et al. | |
| 6,756,480 | B2 * | 6/2004 | Kostenuik et al. | 530/387.1 |

FOREIGN PATENT DOCUMENTS

| | | | |
|---|---|---|---|
| JP | 04-293482 | A | 10/1992 |
| JP | 2002-539828 | A | 11/2002 |
| JP | 2003-524369 | A | 8/2003 |
| JP | 2007-528346 | A | 10/2007 |
| KR | 1020020010363 | A | 2/2002 |
| KR | 1020040081378 | A | 9/2004 |
| WO | WO 96/40731 | * | 12/1996 |
| WO | 97/24137 | A1 | 7/1997 |
| WO | 2004081053 | A1 | 9/2004 |
| WO | 2005/047334 | A1 | 5/2005 |

OTHER PUBLICATIONS

Cunningham-Rundles et al (Journal of Immunological Methods, 152, 1992, p. 177-190).*

Pasut et al (Expert Opinion Ther., 2004, 14(6):859-894).*

Simmons et al (Journal of Immunological Methods, 263, 2002, p. 133-147).*

Cunningham-Rundles, C., Et al., "Biological activities of polyethylene-glycol immunoglobulin conjugates," J. of Immunological Methods, 152, pp. 177-190, 1992.

Bentz, H., et al., "Improved local delivery of TGF-β2 by binding to injectable fibrillar collagen via difuncitional plyehtylene glycol," J. Biomedical Material Research, vol. 39, pp. 539-548, 1998.

International Search Report issued on Jan. 6, 2006 in PCT/KR2005/001233.

Japanese Patent Office, Japanese Office Action issued in corresponding JP Application No. 2008-505221, dated Aug. 2, 2011.

* cited by examiner

*Primary Examiner* — Vanessa L. Ford

(74) *Attorney, Agent, or Firm* — Sughrue Mion, PLLC

(57) ABSTRACT

Disclosed are an Fc fragment modified by a non-peptide polymer, a pharmaceutical composition comprising the Fc fragment modified by the non-peptide polymer as a carrier, a complex of the Fc fragment and a drug via a linker and a pharmaceutical composition comprising such a complex. The Fc fragment modified by a non-peptide peptide according to the present invention lacks immunogenicity and effector functions. Due to these properties, the Fc fragment maintains the in vivo activity of a drug conjugated thereto in high levels, remarkably increases the serum half-life of the drug, and remarkably reduces the risk of inducing immune responses.

13 Claims, 6 Drawing Sheets

10% SDS-PAGE

IMMUNOGLOBULIN FC FRAGMENT MODIFIED BY NON-PEPTIDE POLYMER AND PHARMACEUTICAL COMPOSITION COMPRISING THE SAME

STATEMENT REGARDING SEQUENCE LISTING

The Sequence Listing associated with this application is provided in text format in lieu of a paper copy, and is hereby incorporated by reference into the specification. The name of the text file containing the Sequence Listing is 430156_405USPC_SEQUENCE_LISTING.txt. The text file is 3 KB, was created on Sep. 10, 2008 and is being submitted electronically via EFS-Web.

TECHNICAL FIELD

The present invention relates to an IgG Fc fragment modified by a non-peptide polymer, a pharmaceutical composition comprising the IgG Fc fragment modified by the non-peptide polymer as a carrier, a complex of the Fc fragment and a drug via a linker and a pharmaceutical composition comprising such a complex.

BACKGROUND ART

In the past, a large number of pharmacologists and chemists made efforts to chemically alter and/or modify the in vivo activity of naturally occurring, physiologically active molecules. These efforts associated with physiologically active substances were focused mainly on increasing specific in vivo activity, prolonging in vivo activity, reducing toxicity, eliminating or reducing side effects, or modifying specific physiological activities. When a physiologically active substance is chemically modified, it loses some or most of its physiological activities in many cases. However, in some cases, the modification could result in an increase or change in physiological activity. In this regard, many studies have been focused on chemical modification capable of achieving desired physiological activity, and most studies have involved covalently bonding a physiologically active substance (drug) to a physiologically acceptable carrier.

To stabilize proteins and prevent enzymatic degradation and clearance by the kidney, a polymer having high solubility, such as polyethylene glycol (hereinafter, referred to simply as "PEG"), was conventionally used to chemically modify the surface of a protein drug. Since PEG binds in a non-specific manner to a specific region or various regions of a target protein, it has the effects of increasing protein solubility, stabilizing the protein and preventing protein hydrolysis, and has no specific side effects (Sada et al., *J. Fermentation Bioengineering* 71: 137-139, 1991). However, despite capability to enhance protein stability, this PEG coupling has problems of greatly reducing titers of physiologically active proteins and reducing yield due to PEG's reactivity with proteins decreasing with increasing molecular weight of PEG.

Recently, polymer-protein drug conjugates have been suggested. For example, as described in U.S. Pat. No. 5,738,846, a conjugate can be prepared by linking an identical protein drug to both ends of PEG to improve the activity of the protein drug. Also, as described in International Pat. Publication No. WO 92/16221, two different protein drugs can be linked to both ends of PEG to provide a conjugate having two different activities. However, these methods are not effective in sustaining the activity of protein drugs.

Kinstler et al. reported that a fusion protein prepared by coupling granulocyte-colony stimulating factor (G-CSF) to human albumin has improved stability (Kinstler et al., *Pharmaceutical Research* 12(12): 1883-1888, 1995). However, in this publication, since the modified drug, having a G-CSF-PEG-albumin structure, showed a only about four-fold increase in residence time in the body and a slight increase in serum half-life compared to the single administration of the native G-CSF, it has not been industrialized as an effective long-acting formulation for protein drugs.

An alternative method for improving in vivo stability of physiologically active proteins includes linking a physiologically active protein gene to a gene encoding a protein having high serum stability by genetic recombination and culturing of an animal cell transfected with the recombinant gene to produce a fusion protein. For example, a fusion protein can be prepared by conjugating albumin, known to be most effective in enhancing protein stability, or its fragment to a physiologically active protein of interest by genetic recombination (International Pat. Publication Nos. WO 93/15199 and WO 93/15200, European Pat. Publication No. 413,622). A fusion protein of interferon-alpha and albumin, developed by the Human Genome Science Company and marketed under the trade name ALBUFERON™, has a half-life increased from 5 hours to 93 hours in monkeys, but is problematic in terms of having a greatly decreased in vivo activity less than 5% compared to unmodified interferon-alpha (Osborn et al., J. Phar. Exp. Ther. 303(2): 540-548, 2002).

Recombinant DNA technologies were applied to fuse a protein drug to an immunoglobulin Fc fragment. For example, interferon (Korean Pat. Laid-open Publication No. 2003-9464), and interleukin-4 receptor, interleukin-7 receptor or erythropoietin (EPO) receptor (Korean Pat. Registration No. 249572) were previously expressed in mammals in a form fused to an immunoglobulin Fc fragment. International Pat. Publication No. WO 01/03737 describes a fusion protein comprising a cytokine or growth factor linked to an immunoglobulin Fc fragment through peptide linkage. In addition, U.S. Pat. No. 5,116,964 discloses proteins fused to the amino- or carboxyl-terminal end of an immunoglobulin Fc fragment by genetic recombination. U.S. Pat. No. 5,349,053 discloses a fusion protein comprising IL-2 fused to an immunoglobulin Fc fragment through peptide linkage. Other examples of Fc fusion proteins prepared by genetic recombination include a fusion protein of interferon-beta or its derivative and an immunoglobulin Fc fragment (International Pat. Publication NO. WO 0/23472), and a fusion protein of IL-5 receptor and an immunoglobulin Fc fragment (U.S. Pat. No. 5,712,121), a fusion protein of interferon alpha and the Fc region of immunoglobulin G4 (U.S. Pat. No. 5,723,125), and a fusion protein of CD4 protein and the Fc region of immunoglobulin G2 (U.S. Pat. No. 6,451,313).

However, these Fc fusion proteins, in which a polypeptide/protein is linked to the N- or C-terminal end of an Fc fragment through peptide linkage, are problematic as follows. Recombinant production of an Fc fusion protein can be achieved only by expression of a nucleic acid molecule encoding the Fc fusion protein in a single polypeptide/protein form in a single host cell. Thus, since the entire fusion protein is glycosylated or aglycosylated by this system, fusion is impossible between glycosylated and aglycosylated proteins. Also, these Fc fusion proteins mediate effector functions by the Fc region. Through the effector functions of the Fc region, they fix complements or bind to cells expressing FcRs, leading to lysis of specific cells, and induce the production and secretion of several cytokines inducing inflammation, leading to unwanted inflammation (U.S. Pat. No. 6,656,728; Zheng et al., J. Immunology, 1999, 163:4041-4048; Huang et al., Immunology letters, 2002, 81:49-58). Further, the fusion creates a new amino acid sequence, not present in humans, at a connection region between the Fc region and the protein partner, which could potentially induce immune responses in humans.

Many efforts have been made to prepare an immunoglobulin or immunoglobulin fragment retaining a long serum half-life but being deficient in effector functions. Cole et al. reported that, when amino acid residues of the $C_H2$ region at positions 234, 235 and 237, known to play an important role in binding to Fc receptors, are replaced with alanine to produce an Fc derivative having a reduced binding affinity to Fc receptors, the ADCC activity is inhibited (Cole et al., *J. Immunol.* 159: 3613-3621, 1997). Also, U.S. Pat. No. 5,605,690 discloses a TNFR-IgG1 Fc fusion protein which is prepared by genetic recombination using an IgG1 Fc fragment having amino acid alterations in the complement binding region or receptor binding region of immunoglobulin Fc. However, conspicuous improvement was not achieved by any of these variants. For example, Fc may have increased immunogenicity compared to the native human Fc region due to the presence of unsuitable amino acid residues and may lose preferable Fc functions.

On the other hand, pegylation of immunoglobulins forming antigen-antibody complexes has been introduced, for example, for oral administration (J. Immunological Methods, 1992, 152:177-190) or to prevent the induction of complement reaction by aggregation (Biochimica et Biophysica Acta, 1984, 788:248-255). U.S. Pat. No. 4,732,863 employed a pegylation method in order to reduce immunogenicity of monoclonal antibodies and decrease non-specific binding of the antibodies to Fc receptors. However, such pegylation is carried out in a non-specific modification fashion using PEG having a molecular weight of 1 to 5 kDa to pegylate the entire immunoglobulin. Thus, these pegylation methods are disadvantageous in terms of having difficulty in retaining the Fab functions and controlling the degree of pegylation.

In addition, a site-selective pegylation method was reported, which comprises primary protection via coupling to a ligand, and then pegylation. U.S. Pat. No. 6,548,644 employed such a pegylation method to inhibit the immunogenicity, enhance the solubility and increase the serum half-life of a TNFR-Fc fusion protein. The fusion protein is protected using TNF as a protecting agent and then pegylated, thereby pegylating only sites not participating in ligand binding. When 20% of lysine residues were pegylated using PEG having a molecular weight of 1 to 5 kDa, Fc receptor binding was inhibited. However, this pegylation method has drawbacks as follows: FcRn binding sites can be pegylated, leading to a reduction in serum half-life; protection and deprotection steps are very complicated; and a homogeneous pegylated product is difficult to obtain.

As described above, reported PEG-modification methods are focused on the removal of immunogenicity or inhibition of non-specific Fc receptor binding of therapeutic immunoglobulin or Fc fusion proteins. However, there is no attempt at describing modification of a native or recombinant immunoglobulin Fc fragment by a pegylation method for use as a carrier.

Prior to the present invention, the present inventors found that, when an Fc fragment, which is not the entire immunoglobulin but a peptide fragment, is linked with a drug in a non-fused protein form, it improves the in vivo duration of action of the drug and minimizes a reduction in the in vivo activity of the drug, and submitted patent applications for use of the Fc fragment as a carrier and application thereof (Korean Pat. Application Nos. 10-2004-092780, -092781, -092782 and -092783; International Pat. Application Nos. PCT/KR2004/002942, 002943, 002944 and 002945; submitted on Nov. 13, 2004).

The present inventors found that, when the Fc fragment useful as a carrier is pegylated and used as a carrier, it does not have increased sensitivity to proteolytic enzymes, retains its binding capacity to FcRn but is deficient in binding to FcR I, II, III and C1q, and has a serum half-life similar to that of native Fc.

DISCLOSURE OF THE INVENTION

The present inventors prepared a pegylated Fc fragment in a homogeneous state, and found that linkage of such an Fc fragment to a drug via a linker removes the disadvantages of the Fc fragment as a carrier, immunogenicity and immunotoxicity, enhances the in vivo duration and stability of the conjugated drug, and minimizes a reduction in the in vivo activity of the drug, thereby leading to the present invention, which describes a modified Fc fragment useful as a carrier and its use.

It is therefore an object of the present invention to provide an Fc fragment modified by a non-peptide polymer, which is useful as a drug carrier.

It is another object of the present invention to provide a pharmaceutical composition comprising an Fc fragment modified by a non-peptide polymer as a carrier.

It is a further object of the present invention to provide a complex comprising a non-peptide polymer-modified Fc fragment that is linked to a drug via a linker.

It is yet another object of the present invention to provide a pharmaceutical composition comprising a non-peptide polymer-modified Fc fragment that is linked to a drug via a linker.

It is still another object of the present invention to provide methods of preparing the modified Fc fragment and a complex of such a fragment and a drug.

BRIEF DESCRIPTION OF THE DRAWINGS

The above and other objects, features and other advantages of the present invention will be more clearly understood from the following detailed description taken in conjunction with the accompanying drawings, in which.

BEST MODE FOR CARRYING OUT THE INVENTION

Figure 1:
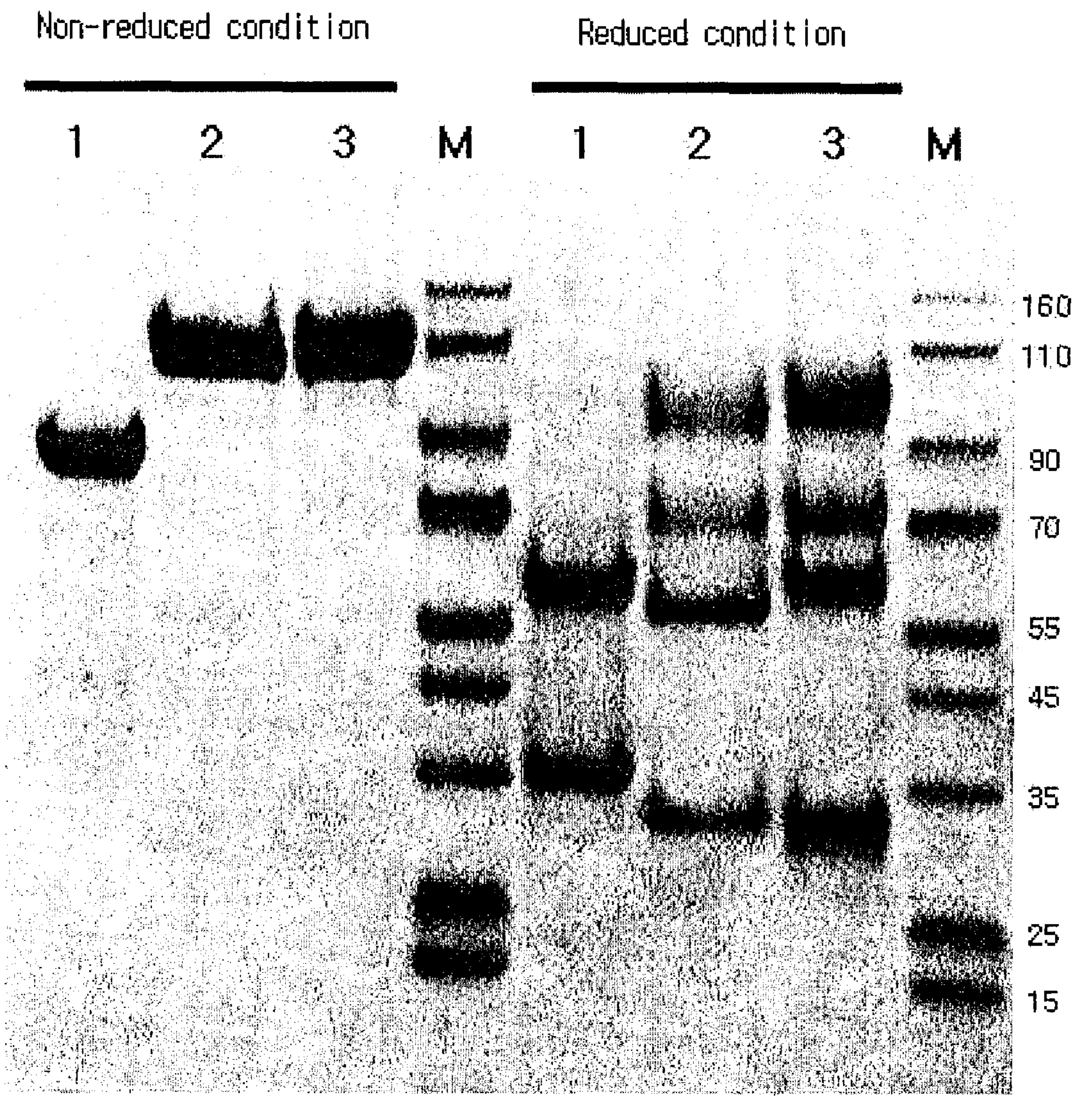
FIG. 1 shows the results of SDS-PAGE of purified IFNα-PEG-G1Fc (lane 1); $^{17}$Ser-G-CSF-PEG-dCysG4Fc (lane 2) and hGH-PEG-dCysG4Fc-20K (lane 3) under non-reduced and reduced conditions (M: molecular size marker)

In one aspect, the present invention relates to an Fc fragment modified by a non-peptide polymer, which is useful as a drug carrier.

The term "carrier," as used herein, refers to a substance linked to a drug. Typically, a complex comprising a drug linked to a carrier greatly decreases the physiological activity of the drug. However, with respect to the objects of the present invention, a carrier is employed in the present invention in order to minimize a decrease in the physiological activity of a drug of interest, linked to the carrier, and reduce immunogenicity of the carrier, thereby enhancing in the in vivo stability of the drug. To accomplish these objects, the present invention employs an Fc fragment modified by a non-peptide polymer as a carrier.

A large number of substances, such as lipids and polymers, were studied to determine their suitability as drug carriers. However, techniques employing an immunoglobulin Fc fragment, not as a portion of a fusion protein but as a drug carrier, are unknown. Prior to the present invention, the present inventors identified that an Fc fragment itself, which is a polypeptide fragment corresponding to a portion of an immunoglobulin protein, is a novel substance having a new usefulness as a drug carrier, which is different from the known usefulness of immunoglobulins (e.g., induction of immune responses by antigen-antibody reactions) (Korean Pat. Application Nos. 10-2004-092780, submitted on Nov. 13, 2004).

In order to reduce the immunogenicity of a carrier while enhancing the in vivo duration of action of a drug linked to the carrier and minimizing the in vivo activity reduction of the drug, the present invention provides particularly an Fc fragment modified by a non-peptide polymer, preferably an IgG or IgM-derived Fc fragment modified by a non-peptide polymer, more preferably an IgG-derived Fc fragment modified by a non-peptide polymer, and particularly preferably, an IgG2 or IgG4-derived Fc fragment modified by a non-peptide polymer.

The term "immunoglobulin G (hereinafter, used interchangeably with "IgG")," as used herein, collectively means proteins that participate in the body's protective immunity by selectively acting against antigens. Immunoglobulins are composed of two identical light chains and two identical heavy chains. The light and heavy chains comprise variable and constant regions. There are five distinct types of heavy chains based on differences in the amino acid sequences of their constant regions: gamma (γ), mu (μ), alpha (α), delta (δ) and epsilon (ε) types, and the heavy chains include the following subclasses: gamma 1 (γ1), gamma 2 (γ2), gamma 3 (γ3), gamma 4 (γ4), alpha 1 (α1) and alpha 2 (α2). Also, there are two types of light chains based on differences in the amino acid sequences of their constant regions: kappa (κ) and lambda (λ) types (Coleman et al., Fundamental Immunology, 2nd Ed., 1989, 55-73). According to the features of the constant regions of the heavy chains, immunoglobulins are classified into five isotypes: IgG, IgA, IgD, IgE and IgM. IgG is divided into IgG1, IgG2, IgG3 and IgG4 subclasses.

Immunoglobulins are known to generate several structurally different fragments, which include Fab, F(ab'), F(ab')2, Fv, scFv, Fd and Fc. Among the immunoglobulin fragments, Fab contains the variable regions of the light chain and the heavy chain, the constant region of the light chain and the first constant region ($C_H1$) of the heavy chain, and has a single antigen-binding site. The Fab' fragments differ from the Fab fragments in terms of having the hinge region containing one or more cysteine residues at the C-terminus (carboxyl terminus) of the heavy chain $C_H1$ domain. The F(ab')2 fragments are produced as a pair of the Fab' fragments by disulfide bonding formed between cysteine residues of the hinge regions of the Fab' fragments. Fv is the minimum antibody fragment that contains only the heavy-chain variable region and the light-chain variable region. The scfv (single-chain Fv) fragments comprise the heavy-chain variable region and the light-chain variable region that are linked to each other by a peptide linker and thus are present in a single polypeptide chain. Also, the Fd fragments comprise only the variable region and $C_H1$ domain of the heavy chain.

The term "Fc fragment", as used herein, is produced when an immunoglobulin (Ig) molecule is digested with papain, and is a region of an immunoglobulin molecule except for the variable region ($V_L$) and the constant regions ($C_L$) of the light chain and the variable region ($V_H$) and the constant region 1 ($C_H1$) of the heavy chain. An Fc fragment is suitable for use as a drug carrier because it is biodegraded in vivo. Also, an Fc fragment is beneficial in terms of preparation, purification and yield of a complex with the Fc fragment because it has a small molecular weight relative to whole immunoglobulin molecules. Further, since the Fab region, which displays high non-homogeneity due to the difference in amino acid sequence between antibodies, is removed, the Fc fragment has greatly increased substance homogeneity and a low potential to induce serum antigenicity. The Fc fragment may further include the hinge region at the heavy-chain constant region. Also, the Fc fragment may be substantially identical to a native form, or may be an extended Fc fragment that contains a portion or the whole of the heavy-chain constant region 1 ($C_H1$) and/or the light-chain constant region 1 ($C_L1$) as long as it has an improved effect. Also, the Fc fragment may be a fragment having a deletion in a relatively long portion of the amino acid sequence of $C_H2$ and/or $C_H3$. A preferred Fc fragment is an IgG or IgM-derived Fc fragment. An IgG-derived Fc fragment is more preferred, and IgG2 Fc and IgG4 Fc fragments are particularly preferred.

The Fc fragment modified according to the present invention may be a combination or hybrid, in detail, a combination or hybrid of Fc fragments derived from IgG, IgA, IgD, IgE and IgM. The term "combination" means a dimeric or multimeric polypeptide in which single-chain Fc fragments of the same origin are linked to a single-chain Fc fragment of a different origin to form a dimer or multimer. The term "hybrid" means a polypeptide in which two or more domains of different origin are present in a single-chain Fc fragment. For example, a hybrid may be composed of one to four domains selected from among $C_H1$, $C_H2$, $C_H3$ and $C_H4$ domains contained in IgG1 Fc, IgG2 Fc, IgG3 Fc and IgG4 Fc.

The Fc fragment modified according to the present invention may be derived from humans or other animals including cows, goats, swine, mice, rabbits, hamsters, rats and guinea pigs, and preferably humans. The human-derived Fc fragment is preferable to a non-human derived Fc fragment, which may act as an antigen in the human body and cause undesirable immune responses such as the production of a new antibody against the antigen.

The Fc fragment modified according to the present invention includes a native amino acid sequence and sequence mutants (variants) thereof. An "amino acid sequence mutant" means to have a different sequence due to a deletion, an insertion, a non-conservative or conservative substitution or combinations thereof of one or more amino acid residues of a native amino acid sequence. Amino acid exchanges in proteins and peptides which do not generally alter the activity of the proteins or peptides are known in the art (H. Neurath, R. L. Hill, The Proteins, Academic Press, New York, 1979). The most commonly occurring exchanges are Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu and Asp/Gly, in both directions. In addition, the Fc fragment, if desired, may be modified by phosphorylation, sulfation, acrylation, glycosylation, methylation, farnesylation, acetylation, amidation, and the like.

The amino acid variant may be a functional equivalent having biological activity identical to a native protein, or, if desired, may be made by altering the property of the native form. For example, the variant may have increased structural stability against heat, pH, etc., or increased solubility alteration and modification of the native amino acid sequence thereof. For example, in an IgG Fc, amino acid residues known to be important in binding, at positions 214 to 238, 297 to 299, 318 to 322, or 327 to 331, may be used as a suitable target for modification. Also, other various derivatives are possible, including one in which a region capable of forming a disulfide bond is deleted, or certain amino acid residues are eliminated at the N-terminal end of a native Fc form or a methionine residue is added thereto. Further, to remove effector functions, a deletion may occur in a complement-binding site, such as a C1q-binding site and an ADCC site. Techniques of preparing such sequence derivatives of the immunoglobulin Fc fragment are disclosed in International Pat. Publication Nos. WO97/34631 and WO96/32478 and the like.

The Fc fragment modified according to the present invention may be obtained from native forms isolated from human and other animals, or may be obtained from transformed animal cells or microorganisms by the recombinant techniques.

The Fc fragment modified according to the present invention may be in the form of having native sugar chains, increased sugar chains compared to a native form or decreased sugar chains compared to the native form, or may be in a deglycosylated form. A glycosylated Fc fragment has a high risk of inducing immune responses due to its stronger complement-dependent cytotoxicity (CDC) activity than an aglycosylated form. Thus, with respect to the present objects, an aglycosylated or deglycosylated Fc fragment is preferred.

As used herein, the term "deglycosylated Fc fragment" refers to an Fc fragment in which sugar moieties are artificially removed, and the term "aglycosylated Fc fragment" means an Fc fragment that is produced in an unglycosylated form by a prokaryote, preferably *E. coli*. The increase, decrease or removal of sugar chains of the Fc fragment may be achieved by methods common in the art, such as a chemical method, an enzymatic method and a genetic engineering method using a microorganism.

A recombinant Fc fragment has increased enzyme sensitivity due to the difference in three dimensional structure from its native form. Also, an aglycosylated IgG is very highly sensitive to proteolytic enzymes (pepsin, chymotrypsin) compared to the native IgG (Morrison et al., J. Immunology, 1989, 143:2595-2601). A recombinant Fc fragment has the same binding affinity to FcRn as does the native Fc produced by papain treatment, but the native Fc fragment has a serum half-life 2 to 3 times longer than that of the recombinant Fc fragment (Eur. J. Immunology, 1999, 29:2819-2825). In the Fc fragment modified according to the present invention, an enzyme cleavage site is protected by a non-peptide polymer. This protection prevents the Fc fragment from being highly sensitive to hydrolases and having reduced serum half-life.

Figure 7:
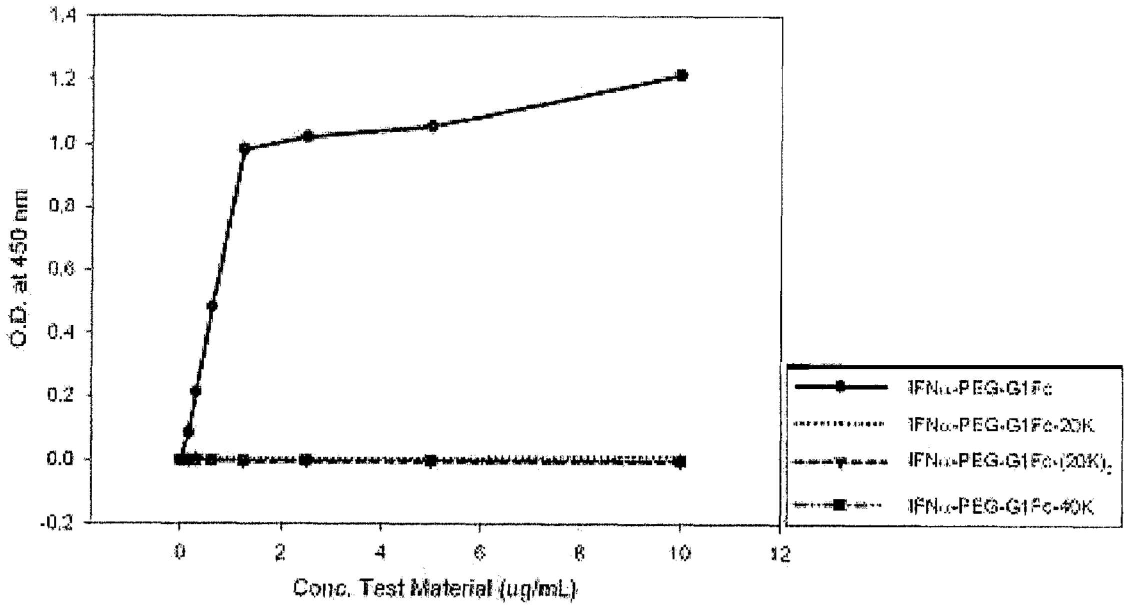
FIG. 7 is a graph showing the results of comparison of native G1Fc, dCysG1Fc, pegylated dCysG1Fc and pegylated dCysG4Fc carrier for binding affinity to the C1q complement.
Figure 8:
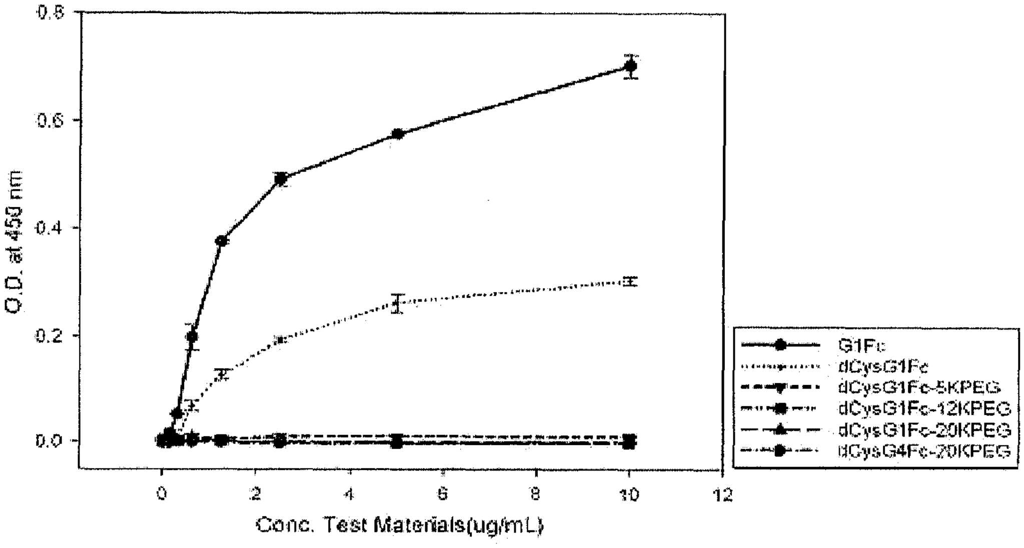
FIG. 8 is a graph showing the results of comparison of IFNα-PEG-G1Fc complex, IFNα-PEG-G1Fc-20K complex, IFNα-PEG-G1Fc-$(20K)_2$ complex and IFNα-PEG-G1Fc-40K complex for binding affinity to the C1q complement.

The deglycosylation remarkably reduces the complement activity of an Fc fragment by about two times or more but does not completely remove the complement activity. However, an Fc fragment modified by a non-peptide polymer had a complete loss of complement activity regardless of glycosylation (FIG. 8). Also, a complex of the non-peptide polymer-modified Fc fragment and a drug was proven to act as a safe drug that does not have effector functions and immunogenicity (FIG. 7). As demonstrated from these results, since the present Fc fragment modified by a non-peptide polymer increases serum half-life of drugs while sustaining the in vivo activity of drugs, as well as rarely having a risk of inducing immune responses, it is very useful as a carrier for drugs such as physiologically active polypeptides.

In another aspect, the present invention relates to a method of modifying an Fc fragment.

In a detailed aspect, the present method comprises reacting an Fc fragment with a non-peptide polymer at a pH of more than 7.0, preferably pH 7.5 to pH 9, and more preferably pH 8.0.

The modification of an Fc fragment may be achieved by pegylation.

The modification of an Fc fragment is performed in a site-selective manner. This is based on the following facts.

(1) An increase in the serum half-life of an Fc fragment depends on the binding affinity of the Fc fragment for FcRn and the sensitivity of the Fc fragment to enzymes. This enzyme sensitivity of the Fc fragment depends on the different amino acid sequences of FcRn binding sites. For example, IgG3 has a serum half-life of 7 days, which is about three times less than the serum half-life of 20 days of IgG1. This shorter serum half-life of IgG3 correlates with reduced binding affinity to FcRn three times relative to IgG1 due to the sequence difference at an FcRn binding site between IgG1 (His435) and IgG3 (Arg435) (Eur. J. Immunology, 1999, 29:2819-2825).

(2) A binding site required for antibody functions of an Fc fragment, that is, ADCC and CDC functions, is located near the hinge region of the Fc $C_H2$ domain, and amino acid residues including Pro331, Lys322, Lys320 and Glu318 directly act in binding to FcR or C1q (JBC, 2001, 276:6591-6604). The binding site for FcRn is located at a junction site between $C_H2$ and $C_H3$ domains in the Fc region, and amino acid residues including His310, Ile253, His435 and His433 form a salt bridge with FcRn (International Immunology, 2001, vol 13, 12:1551-1559).

Since the FcRn binding site is histidine-rich as described above, the interaction between Fc and FcRn occurs in a pH-dependent manner in which binding occurs at less than pH 6.5 and dissociation occurs at more than pH 7.0 (Molecular Cell, 2001, vol 7: 867-877). Thus, modification of His and Lys residues differentially occurs under different optimum pH conditions on the basis of pH 6.5. Since the binding site for FcR I, II and III has a three-dimensional structure different from the binding site for FcRn, most Lys residues in the Fc region are present at the binding site for FcR I, II and III, and the FcRn binding site is His-rich, a region (Lys322 to Lys320) near the hinge region of the $C_H2$ domain is selectively modified at more than 7.0, for example, pH 8.0. In this way, a modified Fc fragment is prepared, which retains the FcRn binding capacity but is deficient in binding to FcR I, II and III and C1q.

The modified Fc fragment prepared according to the above method retains the FcRn binding affinity and has the same serum half-life as does the native Fc fragment but lacks the ability to bind to FcR I, II and III and C1q.

The non-peptide polymer-modified Fc fragment, prepared as described above, serves as a drug carrier. Thus, in a further aspect, the present invention relates to a pharmaceutical composition comprising the Fc fragment modified by a non-peptide polymer as a carrier.

As used herein, the term "non-peptide polymer" modifying an Fc fragment refers to a biocompatible polymer including two or more repeating units linked to each other. Examples of the non-peptide polymer include polyethylene glycol (PEG), polypropylene glycol (PPG), co-poly(ethylene/propylene) glycol, polyoxyethylene (POE), polyurethane, polyphosphazene, polysaccharides, dextran, polyvinyl alcohol, polyvinylpyrrolidones, polyvinyl ethyl ether, polyacryl amide, polyacrylate, polycyanoacrylates, lipid polymers, chitins, hyaluronic acid, and heparin. A preferred non-peptide polymer is polyethylene glycol. The term "pegylation" indicates a process of coupling polyethylene glycol, and with respect to the present objects, means to covalently bind polyethylene glycol to an Fc fragment.

The polymer is linked with an Fc fragment through a specific reactive group. Examples of reactive groups include an aldehyde group, a propionic aldehyde group, a butyl aldehyde group, a maleimide group, a ketone group, a vinyl sulfone group, a thiol group, a hydrazide group, a carbonyldimidazole (CDI) group, a nitrophenyl carbonate (NPC) group, a trysylate group, an isocyanate group, and succinimide derivatives. Examples of succinimide derivatives include succinimidyl propionate (SPA), succinimidyl butanoic acid (SBA), succinimidyl carboxymethylate (SCM), succinimidyl succinamide (SSA), succinimidyl succinate (SS), succinimidyl carbonate, and N-hydroxy succinimide (NHS). Preferably, the polymer is selectively coupled to a lysine residue of an Fc fragment. For this, available is polyethylene glycol having a reactive group that is a succinimide derivative, which is exemplified by succinimidyl propionate, succinimidyl butanoic acid, succinimidyl carboxymethylate, succinimidyl succinamide, succinimidyl succinate, succinimidyl carbonate, and N-hydroxy succinimide. More preferred is polyethylene glycol having a reactive group that is succinimidyl propionate and N-hydroxy succinimide. Lys322 to Lys320 residues, located near the hinge region of the Fc $C_H2$ domain, are selectively pegylated, thereby creating a pegylated Fc fragment that retains the FcRn binding affinity but lacks the binding to FcR I, II and III and C1q.

The Fc fragment and the non-peptide polymer are conjugated to each other at a molar ratio of more than 1:1, preferably 1:1 to 10:1, and more preferably 1:1 to 1:2. To prepare an Fc fragment modified at this ratio, the non-peptide polymer reacts at a molar ratio of more than 1:1. When the Fc fragment is modified by one or more non-peptide polymers, the non-peptide polymers may be the same or different.

Since complement activity of an Fc fragment decreases with the increasing molecular weight and number of polyethylene glycol conjugated to the Fc fragment, polyethylene glycol having a suitable molecular weight should be used. Preferably, polyethylene glycol has a molecular weight of 5 kDa to 50 kDa, and more preferably 10 kDa to 40 kDa. The decreased complement activity of the Fc fragment due to coupling to polyethylene glycol occurs regardless of IgG subtypes or glycosylation.

In yet another aspect, the present invention provides a drug complex in which an Fc fragment modified by a non-peptide polymer is conjugated to a drug via a linker.

As used herein, the term "drug complex", used interchangeably with the term "complex", means a substance in which one or more drugs are conjugated with one or more Fc fragments.

As used herein, the term "drug" refers to a substance displaying therapeutic and preventive activity when administered to humans or animals. Examples of the drug include, but are not limited to, polypeptides, compounds, extracts and nucleic acids. Preferred is a polypeptide drug.

The terms "physiologically active polypeptide drug," "polypeptide drug" and "protein drug" as used herein, are used with the same meanings, and are featured in that they are in a physiologically active form exhibiting antagonistic actions against various in vivo physiological phenomena.

The polypeptide drug has a disadvantage of being unable to sustain physiological action for a long period of time due to its property of being easily denatured or degraded by proteolytic enzymes present in the body. However, when the polypeptide drug is conjugated to the Fc fragment modified according to the present invention to form a complex, the drug has increased structural stability and an increased degradation half-life. Also, the polypeptide conjugated to the Fc fragment has a much smaller decrease in physiological activity than other known polypeptide drug formulations. When IFNα, G-CSF, hGH and other protein drugs are linked to the Fc fragment of the present invention, they displayed an about two- to six-fold increase in serum half-life compared to their conventional forms conjugated to PEG alone or to both of PEG and albumin.

A fusion protein, known prior to the present invention, comprising an Fc fragment and a polypeptide drug that are fused by a recombination method is obtained in such a way that the polypeptide is linked to the N-terminus or C-terminus of the Fc fragment through peptide linkage, and is thus expressed as a single polypeptide from a nucleotide sequence encoding the fusion protein. The linkage of the Fc fragment and a protein drug of the present invention is featured in that it is not a fusion by a conventional recombination method as described above. This brings about a sharp decrease in the activity of the resulting fusion protein because the activity of a protein as a physiologically functional substance is determined by the conformation of the protein. Thus, when a polypeptide drug is fused with Fc by a recombination method, there is no effect with regard to in vivo bioavailability even when the fusion protein has increased structural stability. Also, since such a fusion protein is often misfolded and thus expressed as inclusion bodies, the fusion method is uneconomical in protein production and isolation yield. Further, when the active form of a polypeptide is in a glycosylated form, the polypeptide should be expressed in eukaryotic cells. In this case, Fc is also glycosylated, and this glycosylation may cause unsuitable immune responses in vivo. Only the present invention makes it possible to produce a complex of a glycosylated active polypeptide and an aglycosylated Fc fragment, and overcomes all of the above problems, including improving protein production yield, because the two components of the conjugate are individually prepared and isolated by the best systems.

If the serum half-life needs to be enhanced, any drug may be used without specific limitation as a protein partner of the Fc fragment to form a complex in the present invention. A physiologically active polypeptide is preferably linked to the Fc fragment. Such physiologically active polypeptides include various physiologically active peptides used for treating or preventing human diseases, which are exemplified by hormones, cytokines, enzymes, antibodies, growth factors, transcription regulatory factors, coagulation factors, vaccines, structural proteins, ligand proteins or receptors, cell surface antigens and receptor antagonists, and derivatives and analogues thereof.

In detail, non-limiting examples of the drugs include human growth hormone, growth hormone releasing hormone, growth hormone releasing peptide, interferons and interferon receptors (e.g., interferon-α, -β and -γ, water-soluble type I interferon receptor, etc.), granulocyte colony stimulating factor (G-CSF), granulocyte-macrophage colony stimulating factor (GM-CSF), glucagon-like peptides (e.g., GLP-1, etc.), G-protein-coupled receptor, interleukins (e.g., interleukin-1, -2, -3, -4, -5, -6, -7, -8, -9, -10, -11), -12, -13, -14, -15, -16), -17, -18, -19, -20, -21, -22, -23, -24, -25, -26, -27, -28, -29, -30, etc.) and interleukin receptors (e.g., IL-1 receptor, IL-4 receptor, etc.), enzymes (e.g., glucocerebrosidase, iduronate-2-sulfatase, alpha-galactosidase-A, agalsidase alpha and beta, alpha-L-iduronidase, butyrylcholinesterase, chitinase, glutamate decarboxylase, imiglucerase, lipase, uricase, platelet-activating factor acetylhydrolase, neutral endopeptidase, myeloperoxidase, etc.), interleukin and cytokine binding proteins (e.g., IL-18 bp, TNF-binding protein, etc.), macrophage activating factor, macrophage peptide, B cell factor, T cell factor, protein A, allergy inhibitor, cell necrosis glycoproteins, immunotoxin, lymphotoxin, tumor necrosis factor, tumor suppressors, metastasis growth factor, alpha-1 antitrypsin, albumin, alpha-lactalbumin, apolipoprotein-E, erythropoietin, highly glycosylated erythropoietin, angiopoietins, hemoglobin, thrombin, thrombin receptor activating peptide, thrombomodulin, factor VII, factor VIIa, factor VIII, factor IX, factor XIII, plasminogen activating factor, fibrin-binding peptide, urokinase, streptokinase, hirudin, protein C, C-reactive protein, renin inhibitor, collagenase inhibitor, superoxide dismutase, leptin, platelet-derived growth factor, epithelial growth factor, epidermal growth factor, angiostatin, angiotensin, bone growth factor, bone stimulating protein, calcitonin, insulin, atriopeptin, cartilage inducing factor, elcatonin, connective tissue activating factor, tissue factor pathway inhibitor, follicle stimulating hormone, luteinizing hormone, luteinizing hormone releasing hormone, nerve growth factors (e.g., nerve growth factor, cilliary neurotrophic factor, axogenesis factor-1, brain-natriuretic peptide, glial derived neurotrophic factor, netrin, neurophil inhibitor factor, neurotrophic factor, neuturin, etc.), parathyroid hormone, relaxin, secretin, somatomedin, insulin-like growth factor, adrenocortical hormone, glucagon, cholecystokinin, pancreatic polypeptide, gastrin releasing peptide, corticotropin releasing factor, thyroid stimulating hormone, autotaxin, lactoferrin, myostatin, receptors (e.g., TNFR(P75), TNFR(P55), IL-1 receptor, VEGF receptor, B cell activating factor receptor, etc.), receptor antagonists (e.g., IL1-Ra etc.), cell surface antigens (e.g., CD 2, 3, 4, 5, 7, 11a, 11b, 18, 19, 20, 23, 25, 33, 38, 40, 45, 69, etc.), monoclonal antibodies, polyclonal antibodies, antibody fragments (e.g., scfv, Fab, Fab', F(ab')2 and Fd), and virus derived vaccine antigens.

In particular, preferred as physiologically active polypeptides are those requiring frequent dosing upon administration to the body for therapy or prevention of diseases, which include human growth hormone, interferons (interferon-α, -β, -γ, etc.), granulate colony stimulating factor, erythropoietin (EPO) and antibody fragments.

In addition to the polypeptide drugs, other drugs are also capable of being linked to the Fc fragment modified by a non-peptide polymer in the present invention. Non-limiting examples of these drugs include antibiotics selected from among derivatives and mixtures of tetracycline, minocycline, doxycycline, ofloxacin, levofloxacin, ciprofloxacin, clarithromycin, erythromycin, cefaclor, cefotaxime, imipenem, penicillin, gentamycin, streptomycin, vancomycin, and the like; anticancer agents selected from among derivatives and mixtures of methotrexate, carboplatin, taxol, cisplatin, 5-fluorouracil, doxorubicin, etoposide, paclitaxel, camtotecin, cytosine arabinoside, and the like; anti-inflammatory agents selected from among derivatives and mixtures of indomethacin, ibuprofen, ketoprofen, piroxicam, probiprofen, diclofenac, and the like; antiviral agents selected from among derivatives and mixtures of acyclovir and robavin; and antibacterial agents selected from among derivatives and mixtures of ketoconazole, itraconazole, fluconazole, amphotericin B and griseofulvin.

The "linker" in the complex mediates the linkage of the Fc fragment modified by a non-peptide polymer and the drug. This linker includes peptide and non-peptide linkers. Preferred is a non-peptide linker.

The term "peptide linker", as used herein, means amino acids, and preferably 1 to 20 amino acids, which are linearly linked to each other by peptide bonding. The peptide linker may be in a glycosylated form, but with respect to the present objects, is preferably aglycosylated. This peptide linker is preferably a peptide having a repeating unit of Gly and Ser, which is immunologically inactive for T cells.

The term "non-peptide linker", as used herein, refers to all linkage groups having two or more reactive groups except for the peptide linker. Preferred is a non-peptide polymer. A non-peptide polymer linker used to link the modified Fc fragment to a drug may be exemplified by the aforementioned non-peptide polymers. The non-peptide polymer used as such a linker has reactive groups at both ends, which individually bind to reactive groups of a polypeptide, for example, an amino terminus, a lysine residue, a histidine residue or a cysteine residue. The reactive groups of the polymer include an aldehyde group, a propionic aldehyde group, a butyl aldehyde group, a maleimide group, a ketone group, a vinyl sulfone group, a thiol group, a hydrazide group, a carbonyldimidazole (CDI) group, a nitrophenyl carbonate (NPC) group, a trysylate group, an isocyanate group, and succinimide derivatives. Examples of succinimide derivatives include succinimidyl propionate (SPA), succinimidyl butanoic acid (SBA), succinimidyl carboxymethylate (SCM), succinimidyl succinamide (SSA), succinimidyl succinate (SS), succinimidyl carbonate, and N-hydroxy succinimide (NHS). The reactive groups at both ends of the non-peptide polymer may be the same or different. For example, the non-peptide polymer may have a maleimide group at one end and an aldehyde group at another end.

Low molecular weight chemical binders, such as carbodiimide or glutaraldehyde, have the following problems: they bind simultaneously to several sites on a protein, leading to denaturation of the protein, and bind non-specifically, thus making it difficult to control linking sites or to purify a connected protein. In contrast, the non-peptide polymer used in the present invention has advantages of facilitating the control of linking sites, minimizing non-specific reactions and facilitating protein purification.

The number of drug and linker molecules, capable of being linked to the present Fc fragment modified by a non-peptide polymer, is not particularly limited. Preferably, in the drug complex of the present invention, the drug and the modified Fc fragment may be conjugated to each other at a molar ratio of 1:1 to 10:1, and preferably 1:1 to 2:1.

The linkage of the Fc fragment modified by a non-peptide polymer, a certain linker and a certain drug include all covalent bonds except for a peptide bond formed when the Fc fragment and a polypeptide drug are expressed as a fusion protein by genetic recombination, and all types of non-covalent bonds such as hydrogen bonds, ionic interactions, van der Waals forces and hydrophobic interactions. However, with respect to the physiological activity of the drug, the linkage is preferably made by covalent bonds.

The drug complex may include one or more copies of a unit structure of "drug-linker-Fc fragment modified by a non-peptide polymer", which are preferably linked linearly by covalent bonds. A drug-monomeric, dimeric or multimeric complex may be formed through an Fc fragment by linking one or more drugs to a single Fc fragment, thereby effectively achieving an increase in in vivo activity and stability of drugs.

Figure 3:
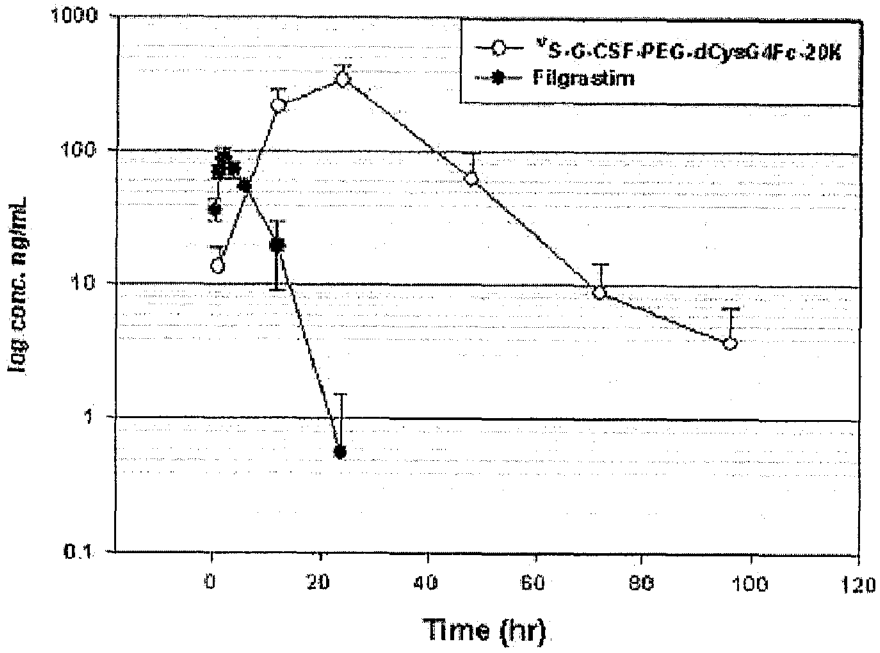
FIG. 3 is a graph showing the results of pharmacokinetic analysis of native G-CSF and $^{17}$Ser-G-CSF-PEG-dCysG4Fc-20K.
Figure 4:
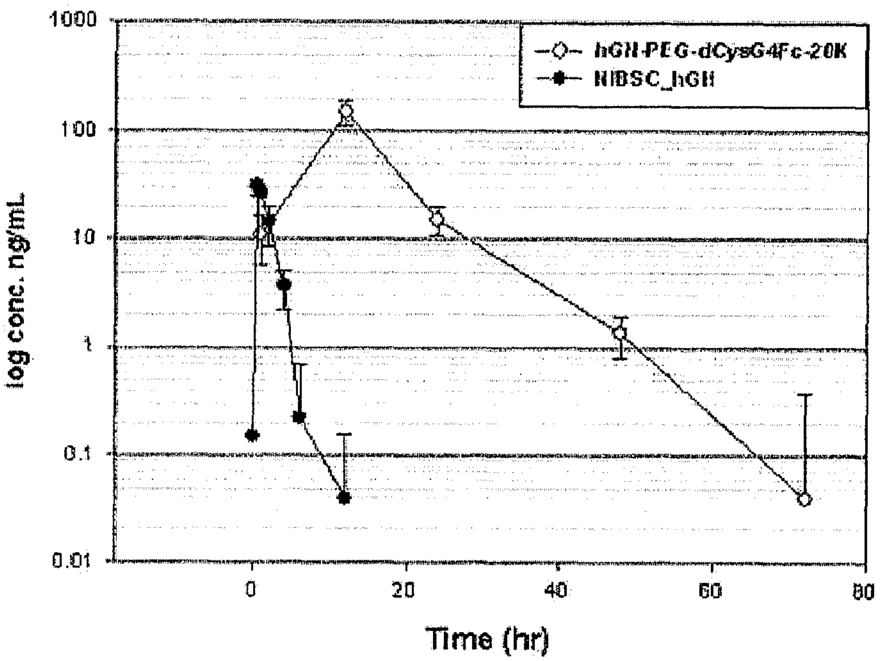
FIG. 4 is a graph showing the results of pharmacokinetic analysis of native hGH and hGH-PEG-dCysG4Fc-20K.
Figure 5:
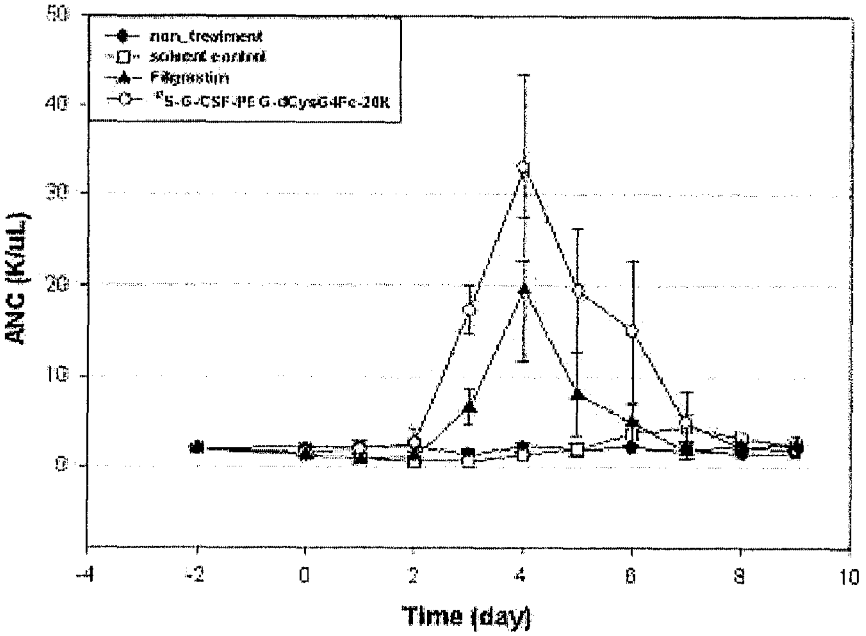
FIG. 5 is a graph showing the in vivo effects of native G-CSF and $^{17}$Ser-G-CSF-PEG-dCysG4Fc-20K.
Figure 6:
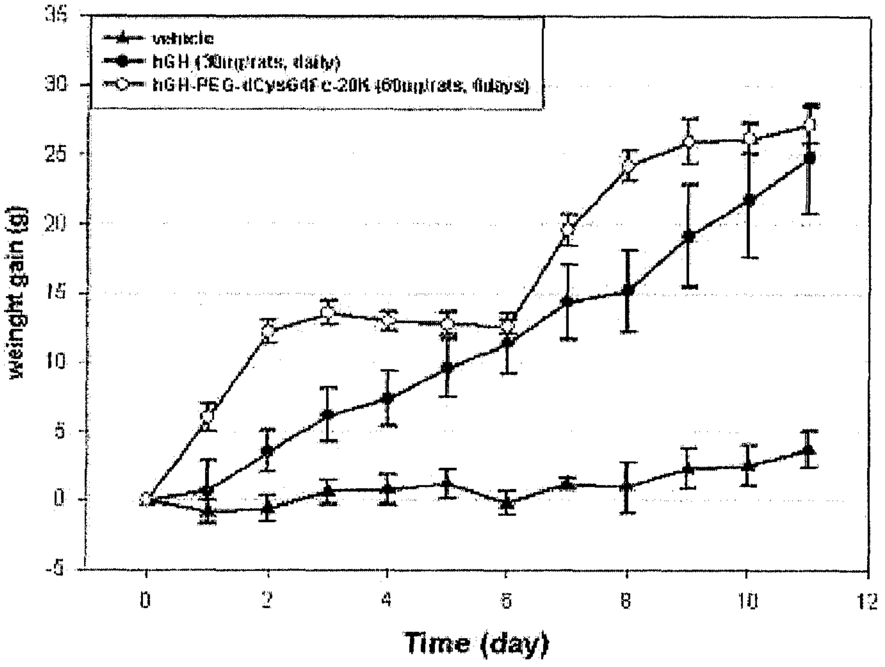
FIG. 6 is a graph showing the in vivo effects of native hGH and hGH-PEG-dCysG4Fc-20K.

In the detailed practice, when a physiologically active polypeptide was linked to a pegylated Fc fragment through polyethylene glycol to form a complex, the serum half-lives of $^{17}$S-G-CSF and hGH increased about five to ten times (FIGS. 3 and 4), and the in vivo activity of the polypeptides increased more than five times (FIGS. 5 and 6). In addition, when a complex, comprising IFN alpha linked to a glycosylated Fc fragment or a glycosylated Fc fragment modified by PEG as a carrier, was assessed for binding affinity to C1q, a complex of a glycosylated Fc and IFNα (IFNα-PEG-G1Fc) maintained high affinity for C1q, whereas all interferon complexes with a glycosylated Fc modified by PEG having a molecular weight of 20 kDa to 40 kDa completely lost the affinity for C1q (FIG. 7).

In still another aspect, the present invention provides a pharmaceutical composition comprising a drug complex in which an Fc fragment modified by a non-peptide polymer is linked to a drug via a linker, the pharmaceutical composition increasing the in vivo duration of action and the stability of the drug.

The pharmaceutical composition may be administered via various routes. The term "administration", as used herein, means introduction of a predetermined amount of a substance into a patient by a certain suitable method. The complex of the present invention may be administered via any of the common routes, as long as it is able to reach a desired tissue. A variety of modes of administration are contemplated, including intraperitoneally, intravenously, intramuscularly, subcutaneously, intradermally, orally, topically, intranasally, intrapulmonarily and intrarectally, but the present invention is not limited to these exemplified modes of administration. However, since peptides are digested upon oral administration, active ingredients of a composition for oral administration should be coated or formulated for protection against degradation in the stomach. Preferably, the present composition may be administered in an injectable form. In addition, the pharmaceutical composition of the present invention may be administered using a certain apparatus capable of transporting the active ingredients into a target cell.

The pharmaceutical composition of the present invention may include a pharmaceutically acceptable carrier. For oral administration, the pharmaceutically acceptable carrier may include binders, lubricants, disintegrators, excipients, solubilizers, dispersing agents, stabilizers, suspending agents, coloring agents and perfumes. For injectable preparations, the pharmaceutically acceptable carrier may include buffering agents, preserving agents, analgesics, solubilizers, isotonic agents and stabilizers. For preparations for topical administration, the pharmaceutically acceptable carrier may include bases, excipients, lubricants and preserving agents. The pharmaceutical composition of the present invention may be formulated into a variety of dosage forms in combination with the aforementioned pharmaceutically acceptable carriers. For example, for oral administration, the pharmaceutical composition may be formulated into tablets, troches, capsules, elixirs, suspensions, syrups or wafers. For injectable preparations, the pharmaceutical composition may be formulated into a unit dosage form, such as a multidose container or an ampule as a single-dose dosage form. The pharmaceutical composition may be also formulated into solutions, suspensions, tablets, capsules and long-acting preparations.

Examples of carriers, excipients and diluents suitable for the pharmaceutical formulations include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oils. In addition, the pharmaceutical formulations may further include fillers, anti-coagulating agents, lubricants, humectants, perfumes, emulsifiers and antiseptics.

The dosage of the pharmaceutical composition of the present invention comprising the Fc fragment modified by a non-peptide polymer as a carrier may be determined by several related factors including the types of diseases, administration routes, the patient's age, gender, weight and severity of the illness, as well as by the types of the drug as an active component. Since the pharmaceutical composition of the present invention has a very long duration in vivo, it has an advantage of greatly reducing administration frequency of pharmaceutical drugs. Also, since the present composition is not immunogenic in vivo, it has a low risk of side effects, can be administered for a long period of time and is safe.

In still another aspect, the present invention provides a method of preparing a drug complex in which an Fc fragment modified by a non-peptide linker is linked to a drug via a linker.

In a detailed aspect, the method comprises:

(a) facilitating a reaction between a linker having a reactive group at both ends thereof, a drug and an Fc fragment modified by a non-peptide polymer to be covalently crosslinked; and (b) isolating a resulting complex in which the drug and the Fc fragment modified by the non-peptide polymer are covalently linked to each end of the linker.

At Step (a), the covalent linkage of the three components occurs sequentially or simultaneously. For example, when the drug and the Fc fragment modified by the non-peptide polymer are linked to each end of the linker, any one of the drug and the Fc fragment modified by the non-peptide polymer is linked to one end of the linker, and the other is then linked to the other end of the linker. This sequential linkage is preferred for minimizing the production of byproducts other than a desired complex.

In detail, Step (a) may include:

(a1) covalently linking an Fc fragment modified by a non-peptide polymer or a drug to one end of a linker;

(a2) isolating a conjugate comprising the Fc fragment modified by the non-peptide polymer or the drug linked to the linker from the reaction mixture; and (a3) covalently linking a drug or an Fc fragment modified by a non-peptide polymer to the other end of the linker of the isolated conjugate to provide a complex comprising the Fc fragment modified by the non-peptide polymer and the drug, which are linked to each end of the linker.

At Step (a1), the optimal reaction molar ratio of the drug and the linker may range from 1:1.25 to 1:5, and the optimal reaction molar ratio of the Fc fragment modified by the non-peptide polymer and the linker may range from 1:5 to 1:10.

On the other hand, at Step (a3), the reaction molar ratio of the conjugate obtained at Step (a2) to the physiologically active polypeptide or Fc fragment modified by the non-peptide polymer may range from 1:0.5 to 1:20, and preferably 1:1 to 1:3.

If desired, Steps (a1) and (a3) may be carried out in the presence of a reducing agent depending on the type of reactive groups at both ends of the linker participating in reactions at Steps (a1) and (a3). Preferred reducing agents may include sodium cyanoborohydride ($NaCNBH_3$), sodium borohydride, dimethylamine borate and pyridine borate.

Taking into consideration purities required at Steps (a2) and (b) and molecular weights and charges of products, a suitable protein isolation method may be selected from methods commonly used for protein isolation in the art. For example, a variety of known methods including size exclusion chromatography and ion exchange chromatography may be applied. If desired, a combination of a plurality of different methods may be used for a high degree of purification.

A better understanding of the present invention may be obtained through the following examples which are set forth to illustrate, but are not to be construed as the limit of the present invention.

EXAMPLE 1

Preparation of Carrier and Pegylated Carrier

<Step 1> Preparation of Native Carrier (Immunoglobulin Fc Fragment) Using Immunoglobulin A native immunoglobulin Fc fragment was prepared as follows. 200 mg of 150-kDa immunoglobulin G (IgG, Green Cross, Korea) dissolved in 10 mM phosphate buffer was treated with 2 mg of a protelytic enzyme, papain (Sigma) at 37° C. for 2 hrs with gentle agitation. After the enzyme reaction, the native immunoglobulin Fc fragment regenerated thus was subjected to chromatography for purification using sequentially a SUPERDEX® column, a protein A column and a cation exchange column. In detail, the reaction solution was loaded onto a SUPERDEX® 200 column (Pharmacia) equilibrated with 10 mM sodium phosphate buffer (PBS, pH 7.3), and the column was eluted with the same buffer at a flow rate of 1 ml/min. Unreacted immunoglobulin molecules (IgG) and F(ab')2, which had a relatively high molecular weight compared to the native immunoglobulin Fc fragment, were removed using their property of being eluted earlier than the native Ig Fc fragment. Fab fragments having a molecular weight similar to the native Ig Fc fragment were eliminated by protein A column chromatography. The resulting fractions containing the native Ig Fc fragment eluted from the Superdex SUPERDEX® 200 column were loaded at a flow rate of 5 ml/min onto a protein A column (Pharmacia) equilibrated with 20 mM phosphate buffer (pH 7.0), and the column was washed with the same buffer to remove proteins unbound to the column. Then, the protein A column was eluted with 100 mM sodium citrate buffer (pH 3.0) to obtain highly pure native immunoglobulin Fc fragment. The Fc fractions collected from the protein A column were finally purified using a cation exchange column (polyCAT, Po1yLC Company), wherein this column loaded with the Fc fractions was eluted with a linear gradient of 0.15-0.4 M NaCl in 10 mM acetate buffer (pH 4.5), thus providing highly pure native Ig Fc fractions.

<Step 2> Preparation of Recombinant Carrier (Immunoglobulin Fc Fragment)

<Preparation of IgG4 Fc Derivative Expression Vector>

To prepare human immunoglobulin IgG4 heavy chain constant regions, a derivative (dCysG4Fc), having a nine amino acid deletion at the amino terminus of the native hinge region, was prepared.

As an expression vector containing an *E. coli* secretory sequence, pT14S1SH-4T20V22Q (Korean Pat. No. 38061), developed prior to the present invention by the present inventor, was used.

To obtain human immunoglobulin IgG4 heavy chain constant regions, RT-PCR was carried out using RNA isolated from human blood cells as a template, as follows. First, total RNA was isolated from about 6 ml of blood using a Qiamp RNA blood kit (Qiagen), and gene amplification was performed using the total RNA as a template and a One-Step RT-PCR kit (Qiagen). In this PCR, a pair of synthesized primers represented by SEQ ID Nos. 1 and 2 and another pair of synthesized primers represented by SEQ ID Nos. 2 and 3 were used. SEQ ID NO. 1 is a nucleotide sequence starting from the 10th residue, serine, of 12 amino acid residues (SEQ ID NO. 9), below, of the hinge region of IgG4. SEQ ID NO. 3 was designed to have a nucleotide sequence encoding a $C_H2$ domain having alanine as a first amino acid residue. SEQ ID NO. 2 was designed to have a BamHI recognition site containing a stop codon. SEQ ID NO. 10 indicates a nucleotide sequence of a sense strand encoding an amino acid sequence corresponding to the IgG4 hinge region, and SEQ ID NO. 11 indicates a nucleotide sequence of an anti-sense strand of the above nucleotide sequence.

```
 1   2   3   4   5   6   7   8   9   10  11  12
gag tcc aaa tat ggt ccc cca tgc cca tca tgc cca   (SEQ ID NO. 10)

ctc agg ttt ata cca ggg ggt acg ggt agt acg ggt   (SEQ ID NO. 11)

Glu Ser Lys Tyr Gly Pro Pro Cys Pro Ser Cys Pro    (SEQ ID NO. 9)
```

To clone each of the amplified IgG4 constant region fragments into an expression vector containing an *E. coli* secretory sequence variant, the pT14S1SH-4T20V22Q (Korean Pat. No. 38061) developed prior to the present invention by the present inventors was used. This expression vector contains a heat-stable enterotoxin secretory sequence derivative that has a nucleotide sequence represented by SEQ ID NO. 4. To facilitate cloning, a StuI restriction enzyme recognition site was inserted into an end of the *E. coli* heat-stable enterotoxin secretory sequence derivative of the pT14S1SH-4T20V22Q plasmid through site-directed mutagenesis using a pair of primers represented by SEQ ID Nos. 5 and 6 to induce mutagenesis to introduce the StuI site at a nucleotide sequence coding for the last amino acid residue of the secretory sequence. This insertion of the StuI site was found to be successful by DNA sequencing. The resulting pT14S1SH-4T20V22Q plasmid containing a StuI site was designated as "pmSTII". The pmSTII plasmid was treated with StuI and BamHI and subjected to agarose gel electrophoresis, and a large fragment (4.7 kb), which contained the *E. coli* heat-stable enterotoxin secretory sequence derivative, was purified. Then, the amplified gene fragments were digested with BamHI and ligated with the linearized expression vector fragment, thus providing pSTIIdCG4Fc and pSTIIG4Mo.

<Preparation of IgG1 Fc Derivative Expression Vector>

To prepare a human immunoglobulin IgG1 heavy chain constant region, a derivative (dCysG1Fc), having a twelve amino acid deletion at the amino terminus of the native hinge region, was prepared. RT-PCR was carried out using a pair of primers of SEQ ID NOS. 7 and 8 according to the same method as described above.

SEQ ID NO. 7 is a nucleotide sequence starting from the 13rd residue, proline, of 15 amino acid residues of the hinge region (Glu Pro Lys Ser Cys Asp Lys Thr His Thr Cys Pro Pro Cys Pro). The gene amplified using the pair of primers represented by SEQ ID NOS. 7 and 8 was designed to contain an amino terminal end starting with the Pro-Cys-Pro sequence of the hinge region and $C_H2$ and $C_H3$ domains, among a whole IgG1 Fc gene sequence.

To clone the amplified IgG1 Fc gene into an expression vector containing an *E. coli* secretary sequence, the aforementioned pmSTII vector was used. According to a cloning procedure similar to that described above, the pmSTII plasmid was treated with StuI and BamHI and subjected to agarose gel electrophoresis, and a large fragment (4.7 kb) was purified, which contained the *E. coli* heat-stable enterotoxin secretary sequence variant. Then, the amplified IgG1 Fc gene was digested with BamHI and ligated with the linearized expression vector, thus providing pSTIIdCG1Fc.

The expression vectors thus constructed were transformed into an expression host cell, *E. coli* BL21(DE3), and the resulting *E. coli* transformants were designated BL21/pSTIIdCG4Fc (HM10932), BL21/pSTIIdCG4Mo (HM10934) and BL21/pSTIIdCG1Fc (HM10927), which was deposited at the Korean Culture Center of Microorganisms (KCCM) on Sep. 15, 2004 and assigned accession numbers KCCM-10597, KCCM-10599 and KCCM-10588. Then, when the cultures reached an $OD_{600}$ value of 80, an inducer, IPTG, was added to the cultures to induce protein expression. The cultures were further cultured for 40 to 45 hrs until the OD value at 600 nm increased to 100 to 120. *E. coli* cells recovered from the fermentation fluid were disrupted to provide cell lysates. The cell lysates were subjected to two-step column chromatography to purify recombinant immunoglobulin constant region derivatives present in the cytosol.

5 ml of a protein-A affinity column (Pharmacia) was equilibrated with PBS, and the cell lysates were loaded onto the column at a flow rate of 5 ml/min. Unbound proteins were washed out with PBS, and bound proteins were eluted with 100 mM citrate (pH 3.0). The collected fractions were desalted using a HiPrep 26/10 desalting column (Pharmacia) with 10 mM Tris buffer (pH 8.0). Then, secondary anion exchange column chromatography was carried out using 50 ml of a Q HP 26/10 column (Pharmacia). The primary purified recombinant aglycosylated immunoglobulin Fc derivative fractions were loaded onto the Q-Sepharose HP 26/10 column, and the column was eluted with a linear gradient of 0-0.2 M NaCl in 10 mM Tris buffer (pH 8.0), thus providing highly pure recombinant aglycosylated immunoglobulin Fc derivative fractions, dCysG4Fc and dCysG1Fc fractions.

<Step 3> Preparation of Pegylated Carriers

Polyethylene glycol succinimidyl propionate (PEG-SPA, mean MWs 5,000, 12,000 and 20,000 Da, Shearwater) and polyethylene glycol N-hydroxysuccinimidyl (PEG-NHS, mean MW 40,000 Da, Shearwater) were individually mixed with 100 mg of native (G1Fc) or recombinant (dCysG4Fc, dCysG1Fc) carriers in 20 ml of 50 mM Tris-HCl buffer (pH 8.0) at a carrier:PEG molar ratio of 1:2. The reaction mixture was allowed to react at 4° C. for 2 hrs, and mono-pegylated carriers and di-pegylated carriers were purified as follows. The reaction mixture was loaded onto a Q-Sepharose HP column (Pharmacia) equilibrated with 10 mM Tris-HCl buffer (pH 7.5) at a flow rate of 10 ml/m. After the column was sufficiently washed with the equilibration buffer, the column was eluted with a linear gradient using 0.5 M NaCl. High purity of mono-pegylated carriers and di-pegylated carriers were eluted sequentially, thus purifying a total of ten carrier derivatives in native forms (mono-pegylated G1Fc and di-pegylated G1Fc) and recombinant forms (mono-pegylated dCysG1Fc and mono-pegylated dCysG4Fc). Mono-pegylated G1Fc was prepared in two forms, G1Fc-20K and G1Fc-40K, and di-pegylated G1Fc in G1Fc-$(20K)_2$ form. Mono-pegylated dCysG1Fc was in three forms, dCysG1Fc-5K, dCysG1Fc-12K and dCysG1Fc-20K, and mono-pegylated dCysG4Fc in dCysG4Fc-20K form (Table 1).

TABLE 1

| No. | Carrier | Fc fragment | PEGylated form |
|---|---|---|---|
| 1 | G1Fc | Native IgG1 | — |
| 2 | G1Fc-20K | Native IgG1 | Mono 20 kDa PEG |
| 3 | G1Fc-$(20K)_2$ | Native IgG1 | Di 20 kDa PEG |
| 4 | G1Fc-40K | Native IgG1 | Mono 40 kDa PEG |
| 5 | dCysG1Fc | Recombinant IgG1 derivative | — |
| 6 | dCysG1Fc-5K | Recombinant IgG1 derivative | Mono 5 kDa PEG |
| 7 | dCysG1Fc-12K | Recombinant IgG1 derivative | Mono 12 kDa PEG |
| 8 | dCysG1Fc-20K | Recombinant IgG1 derivative | Mono 20 kDa PEG |
| 9 | DCysG4Fc | Recombinant IgG1 derivative | — |
| 10 | DCysG4Fc-20K | Recombinant IgG1 derivative | Mono 20 kDa PEG |

EXAMPLE 2

Preparation of Interferon-Peg-Carrier Complexes

<Step 1>Preparation of interferon-PEG conjugate 3.4-kDa polyethylene glycol having an aldehyde reactive group at both ends, ALD-PEG-ALD (Shearwater), was mixed with human interferon alpha-2b (hIFNα-2b, MW: 20 kDa) dissolved in 100 mM phosphate buffer in an amount of 5 mg/ml at an IFNa:PEG molar ratio of 1:1, 1:2.5, 1:5, 1:10 and 1:20. To this mixture, a reducing agent, sodium cyanoborohydride (NaCNBH3, Sigma), was added at a final concentration of 20 mM and was allowed to react at 4° C. for 3 hrs with gentle agitation to allow PEG to link to the amino terminal end of interferon alpha. To obtain a 1:1 conjugate of PEG and interferon alpha, the reaction mixture was subjected to size exclusion chromatography using a SUPERDEX® column (Pharmacia). The IFNa-PEG conjugate was eluted from the column using 10 mM potassium phosphate buffer (pH 6.0) as an elution buffer, and interferon alpha not linked to PEG, unreacted PEG and dimer byproducts where PEG was linked to two interferon alpha molecules were removed. The purified IFNa-PEG conjugate was concentrated to 5 mg/ml. Through this experiment, the optimal reaction molar ratio for IFNa to PEG, providing the highest reactivity and generating the smallest amount of byproducts such as dimers, was found to be 1:2.5 to 1:5.

<Step 2> Preparation of IFNα-PEG-Fc Complexes

To link the IFNα-PEG conjugate purified in the above step 1 to the N-terminus of a native carrier (or pegylated native carrier), the native immunoglobulin Fc fragment (G1Fc, about 53 kDa) prepared in Example 1 was dissolved in 10 mM phosphate buffer and mixed with the IFNα-PEG conjugate at an IFNα-PEG conjugate:Fc molar ratio of 1:1, 1:2, 1:4 and 1:8. After the phosphate buffer concentration of the reaction solution was adjusted to 100 mM, a reducing agent, $NaCNBH_3$, was added to the reaction solution at a final concentration of 20 mM and was allowed to react at 4° C. for 20 hrs with gentle agitation. Through this experiment, the optimal reaction molar ratio for IFNα-PEG conjugate to Fc, providing the highest reactivity and generating the fewest byproducts such as dimers, was found to be 1:2. IFNα-PEG-carrier complexes were prepared according to the same method as described above using native immunoglobulin Fc fragments (G1Fc-20K, G1Fc-$(20K)_2$, G1Fc-40K) modified by mono-20 kDa PEG, di-20 kDa PEG and mono-40 kDa PEG, respectively.

<Step 3> Isolation and Purification of the IFNα-PEG-Carrier Complexes

After the reaction of the above step 2, in order to eliminate unreacted substances and byproducts and purify the IFNα-PEG-carrier protein complexes produced, the reaction mixture was loaded onto a PolyWAX LP column (PolyLC) equilibrated with 10 mM Tris-HCl buffer (pH 7.5). The column was then eluted with a linear gradient of 0-0.3 M NaCl in 10 mM Tris-HCl buffer (pH 7.5) containing 1 M NaCl, thereby purifying the IFNα-PEG-carrier complex. The IFNα-PEG-carrier complex fractions were loaded onto a PolyCAT LP column (PolyLC) equilibrated with 10 mM sodium acetate (pH 4.5), and the column was eluted with a linear gradient of 0-0.5 M NaCl in 10 mM sodium acetate buffer (pH 4.5) using 1 M NaCl, thereby purifying IFNα-PEG-G1Fc, IFNα-PEG-G1Fc-20K, IFNα-PEG-G1Fc-(20K) 2 and IFNα-PEG-G1Fc-40K complexes.

EXAMPLE 3

Preparation of Human Granulocyte Colony Stimulating Factor Derivative ($^{17}$S-G-CSF)-PEG-Recombinant Carrier Complex A $^{17}$S-G-CSF-PEG conjugate was prepared and purified according to the same method as in the step 1 of Example 2, except that drug other than interferon alpha, human granulocyte colony stimulating factor (hG-CSF), was used. The purified $^{17}$S-G-CSF-PEG conjugate was linked to the N-terminus of the pegylated recombinant carrier (dCysG4Fc-20K) prepared in Example 1. The coupling reaction was carried out according to the same method as in the step 2 of Example 2. After the coupling reaction, 50 ml of a Q HP 26/10 column (Pharmacia) was used so as to eliminate unreacted substances and byproducts and purify the $^{17}$S-G-CSF-PEG-dCysG4Fc-20K complex produced. The coupling reaction solution was desalted using a HiPrep 26/10 desalting column (Pharmacia) with 10 mM Tris buffer (pH 8.0). Then, the reaction solution was then loaded onto 50 ml of a Q HP 26/10 column at a flow rate of 8 ml/min, and this column was eluted with a linear NaCl gradient of 0-0.2 M to obtain highly purified $^{17}$S-G-CSF-PEG-dCysG4Fc-20K complex fractions.

EXAMPLE 4

Preparation of hGH-Peg-Recombinant Carrier Complex

Highly pure hGH-PEG-dCysG4Fc-20K complex fractions were obtained according to the same method as in Example 3, using drug other than interferon alpha, human growth hormone (hGH, MW: 22 kDa).

EXPERIMENTAL EXAMPLE 1

Identification and Quantitative Analysis of the Protein Complexes

<1-1> Identification of the Protein Complexes

The protein complexes prepared in the above Examples were analyzed by reduced or non-reduced SDS-PAGE using a 4-20% gradient gel and a 10% gel and ELISA (R&D System).

<1-2>Quantitative analysis of the protein complexes

The protein complexes prepared in the above Examples were quantified by size exclusion chromatography using a HiLoad 26/60 SUPERDEX® 75 column (Pharmacia) and 10 mM potassium phosphate buffer (pH 6.0) as an elution buffer, wherein a peak area of each protein conjugate was compared to that of a control group. Previously quantitatively analyzed standards, IFNa, hGH, 17S-G-CSF and Fc, were individually subjected to size exclusion chromatography, and a conversion factor between a concentration and a peak was determined. A predetermined amount of each protein complex was subjected to the same size exclusion chromatography. By subtracting a peak area corresponding to an immunoglobulin Fc fragment from the thus-obtained peak area, a quantitative value for a physiologically active protein present in each protein complex was determined.

When a physiologically active polypeptide conjugated to Fc was quantitatively analyzed using an antibody specific to the physiologically active polypeptide, the antibody was prevented from binding to the polypeptide, resulting in a value lower than an actual value calculated by the chromatography. In the case of the IFNα-PEG-Fc complex, an ELISA resulted in an ELISA value corresponding to about 30% of an actual value.

<1-3> Evaluation of Purity and Mass of the Protein Complexes

Figure 2A:
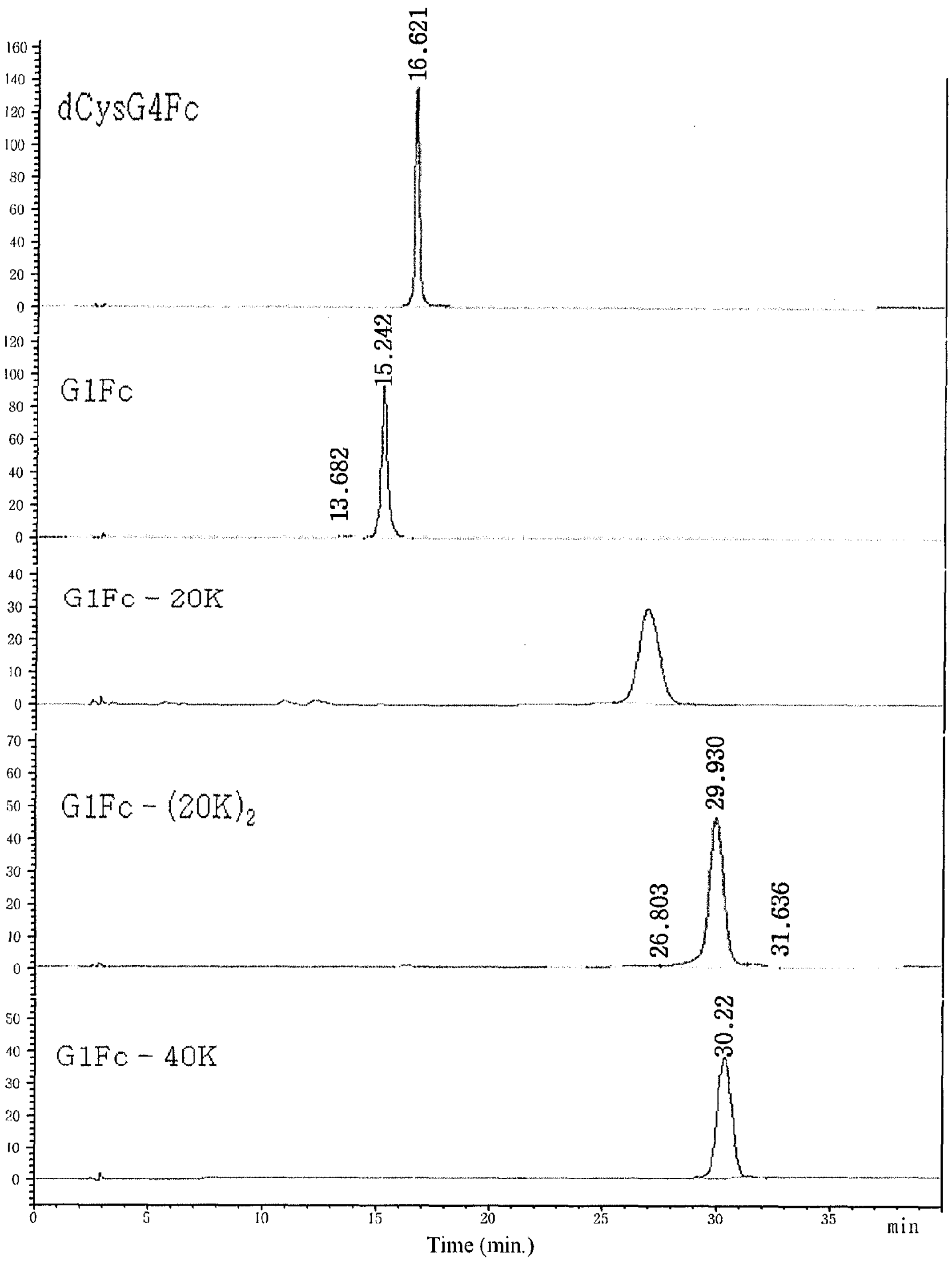
FIGS. 2*a* and 2*b* show the results of reverse phase HPLC for determining the purity of purified carriers (FIG. 2*a*) and complexes (FIG. 2*b*)
Figure 2B:
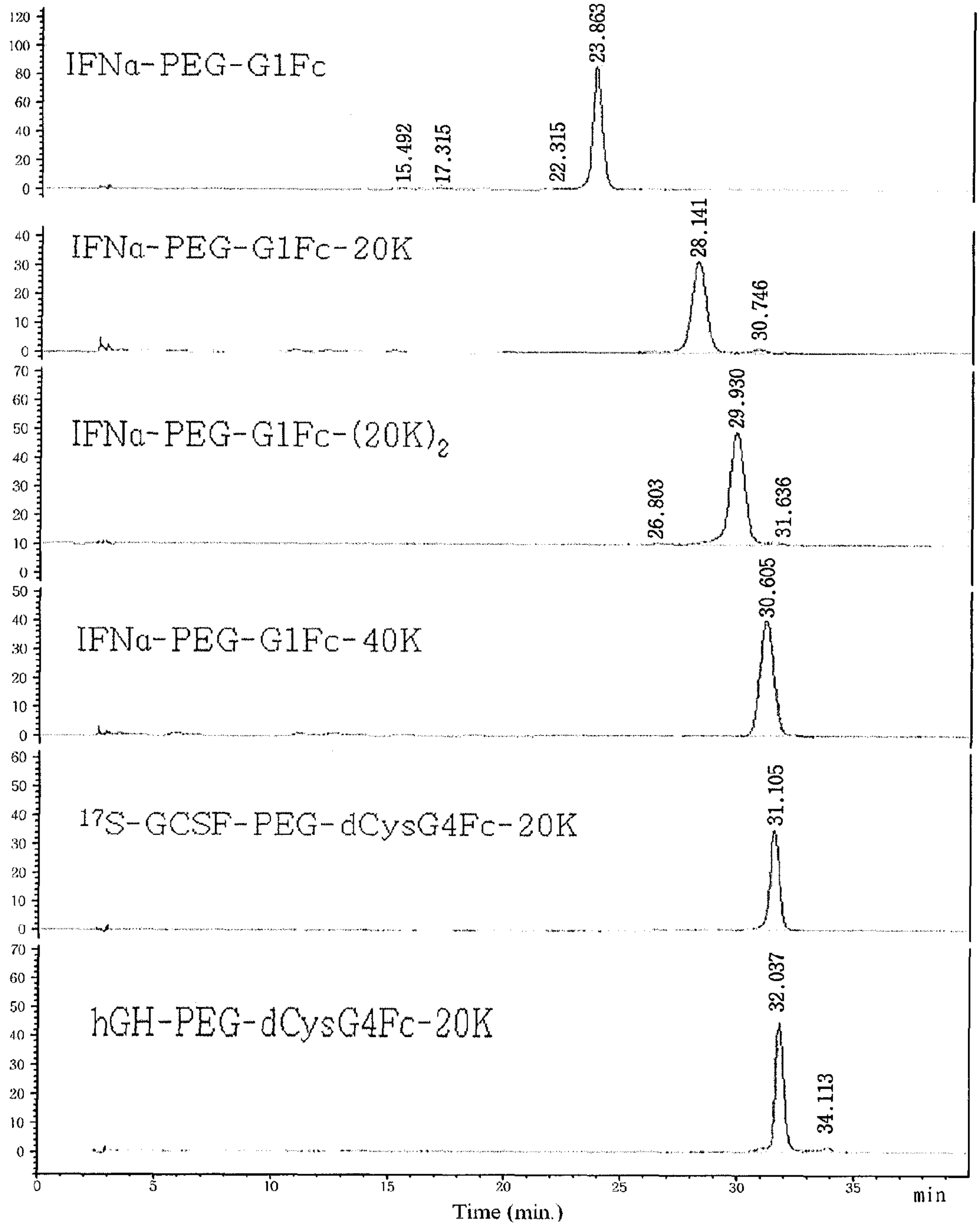

Reverse phase HPLC was carried out to determine purities of the protein complexes prepared in the above Examples, IFNα-PEG-Fc, IFNα-PEG-DG(deglycosylated) Fc and IFNα-PEG-recombinant AG (aglycosylated) Fc derivative. A reverse phase column (259 VHP54 column, Vydac) was used. The column was eluted with a 40-100% acetonitrile gradient with 0.5% TFA, and purities were analyzed by measuring absorbance at 280 nm. As a result, as shown in FIG. 2, the samples contain no unbound interferon or immunoglobulin Fc, and all of the protein complexes, IFNα-PEG-G1Fc, $^{17}$S-G-CSF-dCysG4Fc-20K and hGH-PEG-dCysG4Fc-20K, were found to have a purity greater than 96%.

To determine accurate molecular weights of the purified protein complexes, mass for each complex was analyzed using a high-throughput MALDI-TOF mass spectrophotometer (Voyager DE-STR, Applied Biosystems). Sinapinic acid was used as a matrix. 0.5 μl of each test sample was coated onto a sample slide and air-dried, again mixed with the equal volume of a matrix solution and air-dried, and introduced into an ion source. Detection was carried out in a positive fashion using a linear mode TOF analyzer. Ions were accelerated with a split extraction source operated with delayed extraction (DE) using a delayed extraction time of 750 nsec to 1500 nsec at a total acceleration voltage of about 2.5 kV.

The molecular weights observed by MALDI-TOF mass spectrometry for the Fc protein complexes prepared in Examples are given in Table 2, below. As a result, the obtained protein complex was found to have a purity of more than 95% and a molecular weight very close to a theoretical MW. Also, IFN, $^{17}$S-G-CSF and hGH were found to individually couple to the immunoglobulin Fc fragment at a ratio of 1:1.

TABLE 2

| | Theoretical MW (kDa) | Measured MW (kDa) |
|---|---|---|
| IFNα-PEG-G1Fc (E. 2) | 75.4 | 75.9 |
| IFNα-PEG-G1Fc-20K (E. 2) | 95.4 | 95.9 |
| IFNα-PEG-G1Fc-$(20K)_2$ (E. 2) | 115.4 | 115.9 |
| IFNα-PEG-G1Fc-40K (E. 2) | 115.4 | 115.7 |
| hGH-PEG-dCysG4Fc-20K (E. 3) | 94.9 | 95.0 |
| $^{17}$S-G-CSF-PEG-dCysG4Fc-20K (E. 4) | 91.5 | 91.5 |

EXPERIMENTAL EXAMPLE 2

Pharmacokinetic Analysis

Native forms of physiologically active proteins (controls) and the protein complexes prepared in Examples 3 and 4 were evaluated for serum stability and pharmacokinetic parameters in SD rats (five rats per group). The controls, and the $^{17}$S-G-CSF-PEG-dCysG4Fc-20K complex and the hGH-PEG-G4Fc-20K complex (test groups) were individually injected subcutaneously at a dose of 100 μg/kg. After the subcutaneous injection, blood samples were collected at 0.5, 1, 2, 4, 6, 12, 24, 30, 48, 72 and 96 hrs in the control groups, and in the test groups, at 1, 6, 12, 24, 30, 48, 72, 96, 120, 240 and 288 hrs. The blood samples were collected in tubes with an anticoagulant, heparin, and centrifuged for 5 min using an Eppendorf high-speed micro centrifugator to remove blood cells. Serum protein levels were measured by ELISA using antibodies specific to the physiologically active proteins.

The results of pharmacokinetic analyses are given in Tables 3 and 4, below. In the following tables, $T_{max}$ indicates the time taken to reach the maximal drug serum concentration, $T_{1/2}$ indicates the serum half-life of a drug, and MRT (mean residence time) indicates the mean time that a drug molecule resides in the body.

TABLE 3

| | Native G-CSF (Filgrastim) | $^{17}$S-G-CSF-PEG-dCysG4Fc-20K |
|---|---|---|
| $C_{max}$ (ng/ml) | 87.6 | 397.3 |
| $T_{max}$ (hr) | 2 | 24 |
| $T_{1/2}$ (hr) | 1.28 | 10.52 |
| AUC (ng × hr/ml) | 455 | 12194 |
| MRT (hr) | 6.0 | 25.9 |

TABLE 4

| | NIBSC hGH | hGH-PEG-dCysG4Fc-20K |
|---|---|---|
| $C_{max}$ (ng/ml) | 30.4 | 156.7 |
| $T_{max}$ (hr) | 0.5 | 12 |
| $T_{1/2}$ (hr) | 0.8 | 4.4 |
| AUC (ng × hr/ml) | 64.4 | 3033 |
| MRT (hr) | 1.6 | 17.3 |

As shown from the data of Table 3 for pharmacokinetic analysis of G-CSF and its derivative, the $^{17}$S-G-CSF-PEG-dCysG4Fc-20K complex had a serum half-life about 10-fold longer than did the native G-CSF (filgrastim). The increasing effect of the immunoglobulin Fc fragment on blood circulation time of proteins was maintained in the G-CSF derivative in which some amino acid residues of the hinge region are removed and the $C_H2$ domain is modified by PEG. These results indicate that pegylation does not affect the $C_H3$ domain that is an FcRn binding site, and that the pegylated complex retains the effect of enhancing the serum half-life of a drug.

The enhancing effect of the Fc fragment on serum half-life was also found in cases using hGH. As shown in Table 4, the hGH-PEG-dCysG4Fc-20K complex had a serum half-life about 5-fold longer and a MRT 10-fold higher than the native hGH.

EXPERIMENTAL EXAMPLE 3

Complement-Dependent Cytotoxicity (CDC) Assay

To determine whether the derivatives prepared in the above Examples and proteins corresponding to the constant regions of immunoglobulins, expressed in the *E. coli* transformants and purified, bind to human C1q, an enzyme linked immunosorbent assay (ELISA) was carried out as follows. As test groups, immunoglobulin constant regions produced by the HM10932 and HM10927 transformants and the derivatives prepared in the above Examples were used. As a standard, a glycosylated immunoglobulin (IVIG-globulin S, Green Cross PBM) was used. The test and standard samples were prepared in 10 mM carbonate buffer (pH 9.6) at a concentration of 1 μg/ml. The samples were aliquotted into a 96-well plate (Nunc) in an amount of 200 ng per well, and the plate was coated overnight at 4° C. Then, each well was washed with PBS-T (137 mM NaCl, 2 mM KCl, 10 mM $Na_2HPO_4$, 2 mM $KH_2PO_4$, 0.05% Tween 20) three times, blocked with 250 μl of a blocking buffer (1% bovine serum albumin in PBS-T) at room temperature for 1 hr, and washed again with the same PBS-T three times. The standard and test samples were diluted in PBS-T to a predetermined concentration and added to antibody-coated wells, and the plate was incubated at room temperature for 1 hr and washed with PBS-T three times. Thereafter, 2 μg/ml C1q (R&D Systems) was added to the plate and reacted at room temperature for 2 hrs, and the plate was washed with PBS-T six times. 200 μl of a 1:1000 dilution of a human anti-human C1q antibody-peroxidase conjugate (Biogenesis, USA) in the blocking buffer was added to each well and reacted at room temperature for 1 hr. After each well was washed with PBS-T three times, equal volumes of color reagents A and B (Color A: stabilized peroxide) and Color B: stabilized chromogen; DY 999, R&D Systems) were mixed, and 200 μl of the mixture was added to each well, followed by incubation for 30 min. Then, 50 μl of a reaction termination solution, 2 M sulphuric acid, was added to each well. The plate was read using a microplate reader (Molecular Device). Absorbance of standard and test samples was measured at 450 nm, and the results are given in FIGS. 7 and 8, respectively.

When immunoglobulin Fc fragment was assessed for complement activity according to their glycosylation and pegylation, deglycosylation remarkably reduced about two times the complement activity of the Fc fragment. Pegylation resulted in a decrease in complement activity, and no difference in this decrease was found between dCysG1Fc and dCysG4Fc subtypes. The complement activity decreased as the molecular weights of PEG increased. When the PEG used had a molecular weight of more than 12 kDa, the complement activity was completely removed (FIG. 8).

To determine whether the carrier maintains the property of having no binding affinity to C1q even after being conjugated to a physiologically active peptide, IFN alpha-Fc complexes were prepared using glycosylated Fc and glycosylated Fc modified by PEG as carriers for IFN alpha and were evaluated for their binding affinity to C1q. A glycosylated Fc-coupled IFN alpha complex (IFNα-PEG-G1Fc) retained the high binding affinity to C1q. In contrast, when interferon alpha was coupled to glycosylated Fc modified by PEG having a molecular weight of 20 kDa to 40 kDa, the resulting interferon complexes all completely lost the binding affinity to C1q, thereby demonstrating that the pegylated Fc derivatives are safe carriers lacking effector functions (FIG. 7).

Industrial Applicability

The pharmaceutical composition of the present invention, comprising an Fc fragment modified by a non-peptide polymer as a carrier, increases the serum half-life of a drug conjugated to the Fc fragment, maintains the blood circulation time of the drug, and minimizes a reduction in in vivo activity of the drug. Also, the present pharmaceutical composition overcomes the most significant problems of conventional long-acting formulations, immunogenicity and toxicity of the immunoglobulin Fc fragment, and thus has no risk of inducing immune responses. Due to these advantages, the present pharmaceutical composition is useful for developing safe long-acting formulations of protein drugs. Further, the long-acting formulations of protein drugs according to the present invention are capable of reducing the patient's pain from frequent injections, and maintaining serum concentrations of active polypeptides for a prolonged period of time, thus stably providing pharmaceutical efficacy.

Further, the present method of preparing a drug complex using an Fc fragment modified by a non-peptide polymer overcomes disadvantages of fusion protein production by genetic manipulation, including difficult establishment of expression systems, glycosylation different from a native form, immune response induction and limited orientation of protein fusion, low yields due to non-specific reactions, and problems of chemical coupling such as toxicity of chemical compounds used as binders, thereby easily economically providing protein drugs with extended serum half-life and high activity.

The invention claimed is:

1. A complex consisting of:

an immunoglobulin Fc fragment coupled to a non-peptide polymer, said non-peptide polymer having a reactive group at one end thereof and being coupled to the immunoglobulin Fc fragment via the reactive group, a non-peptide linker having a reactive group at both ends thereof, and a drug, wherein said immunoglobulin Fc fragment coupled to a non-peptide polymer is covalently linked to the drug through the non-peptide linker, wherein the reactive group at one of the ends of the non-peptide linker is coupled to the Fc fragment and the reactive group at the other end of the non-peptide linker is coupled to the drug.

2. The complex as set forth in claim 1, wherein the Fc fragment is an Fc fragment of IgG, IgA, IgD, IgE, or IgM; an Fc fragment of a combination of two or more of IgG, IgA, IgD, and IgE; or an Fc fragment of a hybrid of two or more of IgG, IgA, IgD, and IgE.

3. The complex as set forth in claim 2, wherein the Fc fragment is an Fc fragment of IgG1, IgG2, IgG3, or IgG4; an Fc fragment of a combination of two or more of IgG1, IgG2, IgG3, and IgG4; or an Fc fragment of a hybrid of two or more IgG1, IgG2, IgG3, and IgG4.

4. The complex as set forth in claim 3, wherein the Fc fragment is an IgG4 Fc fragment.

5. The complex as set forth in claim 1, wherein the Fc fragment is aglycosylated.

6. The complex as set forth in claim 1, wherein the non-peptide linker is selected from the group consisting of polyethylene glycol, polypropylene glycol, copoly (ethylene/propylene) glycol, polyoxyethylene, polyurethane, polyphosphazene, polysaccharides, dextran, polyvinyl alcohol, polyvinylpyrrolidones, polyvinyl ethyl ether, polyacryl amide, polyacrylate, polycyanoacrylates, lipid polymers, chitins, hyaluronic acid, heparin, and combinations thereof.

7. The complex as set forth in claim 6, wherein the non-peptide linker is polyethylene glycol.

8. The complex as set forth in claim 1, wherein the drug is a physiologically active polypeptide.

9. The complex as set forth in claim 8, wherein the physiologically active polypeptide is selected from the group consisting of hormones, cytokines, enzymes, antibodies, growth factors, transcription regulatory factors, coagulation factors, vaccines, structural proteins, ligand proteins, receptors, cell surface antigens and receptor antagonists.

10. The complex as set forth in claim 9, wherein the physiologically active polypeptide is selected from the group consisting of human growth hormone, growth hormone releasing hormone, growth hormone releasing peptide, interferons, interferon receptors, colony stimulating factors, glucagon-like peptides, Gprotein-coupled receptor, interleukins, interleukin receptors, enzymes, interleukin binding proteins, cytokine binding proteins, macrophage activating factor, macrophage peptide, B cell factor, T cell factor, protein A, allergy inhibitor, cell necrosis glycoproteins, immunotoxin, lymphotoxin, tumor necrosis factor, tumor suppressors, metastasis growth factor, alpha-1 antitrypsin, albumin, alpha-lactalbumin, apolipoprotein-E, erythropoietin, highly glycosylated erythropoietin, angiopoietins, hemoglobin, thrombin, thrombin receptor activating peptide, thrombomodulin, factor VII, factor VIIa, factor VIII, factor IX, factor XIII, plasminogen activating factor, fibrin-binding peptide, urokinase, streptokinase, hirudin, protein C, C-reactive protein, renin inhibitor, collagenase inhibitor, superoxide dismutase, leptin, platelet-derived growth factor, epithelial growth factor, epidermal growth factor, angiostatin, angiotensin, bone growth factor, bone stimulating protein, calcitonin, insulin, atriopeptin, cartilage inducing factor, elcatonin, connective tissue activating factor, tissue factor pathway inhibitor, follicle stimulating hormone, luteinizing hormone, luteinizing hormone releasing hormone, nerve growth factors, parathyroid hormone, relaxin, secretin, sornatornedin, insulin-like growth factor, adrenocortical hormone, glucagon, cholecystokinin, pancreatic polypeptide, gastrin releasing peptide, corticotropin releasing factor, thyroid stimulating hormone, autotaxin, lactoferrin, myostatin, receptors, receptor antagonists, cell surface antigens, monoclonal antibodies, polyclonal antibodies, and antibody fragments.

11. The complex as set forth in claim 10, wherein the physiologically active polypeptide is selected from the group consisting of human growth hormone, colony stimulating factors, interferon-alpha and erythropoietin.

12. A pharmaceutical composition for increasing in vivo duration of action and in vivo stability of a drug, comprising the complex of claim 1 and a pharmaceutically acceptable carrier.

13. The complex as set forth in claim 1, wherein the Fc fragment is coupled to one or more non-peptide polymers.

* * * * *

SEQUENCE LISTING

```
<160> NUMBER OF SEQ ID NOS: 11

<210> SEQ ID NO 1
<211> LENGTH: 35
<212> TYPE: DNA
<213> ORGANISM: Artificial Sequence
<220> FEATURE:
<223> OTHER INFORMATION: primer for amplification of IgG4 constant
      region

<400> SEQUENCE: 1

cgtcatgccc agcacctgag ttcctggggg gacca                                35


<210> SEQ ID NO 2
<211> LENGTH: 42
<212> TYPE: DNA
<213> ORGANISM: Artificial Sequence
<220> FEATURE:
<223> OTHER INFORMATION: primer for amplification of IgG4 constant
      region

<400> SEQUENCE: 2

gggggatcct catttaccca gagacaggga gaggctcttc tg                        42


<210> SEQ ID NO 3
<211> LENGTH: 29
<212> TYPE: DNA
<213> ORGANISM: Artificial Sequence
<220> FEATURE:
<223> OTHER INFORMATION: primer for amplification of IgG4 constant
      region

<400> SEQUENCE: 3

cggcacctga gttcctgggg ggaccatca                                       29


<210> SEQ ID NO 4
<211> LENGTH: 69
<212> TYPE: DNA
<213> ORGANISM: Escherichia coli

<400> SEQUENCE: 4

atgaaaaaga caatcgcatt tcttcttgca tctatgttcg ttttttctat tgctacaaat     60

gcccaggcg                                                             69
```

-continued

<210> SEQ ID NO 5
<211> LENGTH: 45
<212> TYPE: DNA
<213> ORGANISM: Artificial Sequence
<220> FEATURE:
<223> OTHER INFORMATION: primer for site-directed mutagenesis of
enterotoxin signal sequence

<400> SEQUENCE: 5
tctattgcta caaatgccca ggccttccca accattccct tatcc 45

<210> SEQ ID NO 6
<211> LENGTH: 45
<212> TYPE: DNA
<213> ORGANISM: Artificial Sequence
<220> FEATURE:
<223> OTHER INFORMATION: primer for site-directed mutagenesis of
enterotoxin signal sequence

<400> SEQUENCE: 6
agataacgat gtttacgggt ccggaagggt tggtaaggga atagg 45

<210> SEQ ID NO 7
<211> LENGTH: 33
<212> TYPE: DNA
<213> ORGANISM: Artificial Sequence
<220> FEATURE:
<223> OTHER INFORMATION: primer for amplificaiton of IgG1 constant
region

<400> SEQUENCE: 7
cgccgtgccc agcacctgaa ctcctggggg gac 33

<210> SEQ ID NO 8
<211> LENGTH: 33
<212> TYPE: DNA
<213> ORGANISM: Artificial Sequence
<220> FEATURE:
<223> OTHER INFORMATION: primer for amplification of IgG1 constant
region

<400> SEQUENCE: 8
gggggatcct catttacccg gagacaggga gag 33

<210> SEQ ID NO 9
<211> LENGTH: 12
<212> TYPE: PRT
<213> ORGANISM: homo sapiens
<220> FEATURE:
<221> NAME/KEY: SITE
<222> LOCATION: (1)..(12)
<223> OTHER INFORMATION: hinge region ofIgG4 constant region

<400> SEQUENCE: 9

Glu Ser Lys Tyr Gly Pro Pro Cys Pro Ser Cys Pro
1 5 10

<210> SEQ ID NO 10
<211> LENGTH: 36
<212> TYPE: DNA
<213> ORGANISM: homo sapiens

<400> SEQUENCE: 10
gagtccaaat atggtccccc atgcccatca tgccca 36

<210> SEQ ID NO 11
<211> LENGTH: 36

-continued

```
<212> TYPE: DNA
<213> ORGANISM: homo sapiens

<400> SEQUENCE: 11

tgggcatgat gggcatgggg gaccatattt ggactc                              36
```